United States Patent
Sharma et al.

(10) Patent No.: US 12,090,195 B2
(45) Date of Patent: Sep. 17, 2024

(54) COMBINATION VACCINE COMPOSITION COMPRISING REDUCED DOSE INACTIVATED POLIOVIRUS AND METHOD FOR PREPARING THE SAME

(71) Applicant: SERUM INSTITUTE OF INDIA PRIVATE LTD, Pune Maharashtra (IN)

(72) Inventors: Inder Jit Sharma, Pune Maharashtra (IN); Rakesh Kumar, Pune Maharashtra (IN); Jaganathan Semburakkiannan Kilvani, Pune Maharashtra (IN); Manohar Doddapaneni, Pune Maharashtra (IN); Anil Vyankatrao Shitole, Pune Maharashtra (IN)

(73) Assignee: Serum Institute of India Private Limited, Pune Maharashtra (IN)

( * ) Notice: Subject to any disclaimer, the term of this patent is extended or adjusted under 35 U.S.C. 154(b) by 624 days.

(21) Appl. No.: 17/284,529

(22) PCT Filed: Oct. 4, 2019

(86) PCT No.: PCT/IN2019/050737
§ 371 (c)(1),
(2) Date: Apr. 12, 2021

(87) PCT Pub. No.: WO2020/075184
PCT Pub. Date: Apr. 16, 2020

(65) Prior Publication Data
US 2021/0346483 A1    Nov. 11, 2021

(30) Foreign Application Priority Data
Oct. 12, 2018    (IN) .............................. 201821038850

(51) Int. Cl.
| | | |
|---|---|---|
| *A61K 39/00* | (2006.01) | |
| *A61K 39/102* | (2006.01) | |
| *A61K 39/13* | (2006.01) | |
| *A61K 39/29* | (2006.01) | |
| *A61K 39/295* | (2006.01) | |
| *A61K 47/10* | (2017.01) | |
| *A61K 47/14* | (2017.01) | |
| *A61P 31/04* | (2006.01) | |
| *A61P 31/12* | (2006.01) | |
| *C12N 7/00* | (2006.01) | |
| *A61K 39/10* | (2006.01) | |

(52) U.S. Cl.
CPC ........ *A61K 39/0018* (2013.01); *A61K 39/102* (2013.01); *A61K 39/13* (2013.01); *A61K 39/292* (2013.01); *A61K 39/295* (2013.01); *A61K 47/10* (2013.01); *A61K 47/14* (2013.01); *A61P 31/04* (2018.01); *A61P 31/12* (2018.01); *C12N 7/00* (2013.01); *A61K 2039/10* (2013.01); *A61K 2039/521* (2013.01); *A61K 2039/5252* (2013.01); *A61K 2039/55505* (2013.01); *A61K 2039/6037* (2013.01); *A61K 2039/70* (2013.01)

(58) Field of Classification Search
None
See application file for complete search history.

(56) References Cited

U.S. PATENT DOCUMENTS

| | | | |
|---|---|---|---|
| 6,790,445 B1 | 9/2004 | Ng et al. | |
| 11,179,453 B2* | 11/2021 | Kumar | A61K 39/00 |
| 2004/0258700 A1 | 12/2004 | Frimann | |
| 2011/0256182 A1* | 10/2011 | Zhang | C12N 7/00 435/69.3 |
| 2014/0004150 A1* | 1/2014 | Wang | A61K 39/12 424/234.1 |
| 2021/0346483 A1* | 11/2021 | Sharma | C12N 7/00 |

FOREIGN PATENT DOCUMENTS

| | | | |
|---|---|---|---|
| WO | 2010046934 A1 | | 4/2010 |
| WO | WO 2010/046934 | * | 4/2010 |
| WO | 2012093406 A2 | | 7/2012 |
| WO | 2017048038 A1 | | 3/2017 |
| WO | 2019016654 A1 | | 1/2019 |

OTHER PUBLICATIONS

Liang, Gang. "Iron uptake, signaling, and sensing in plants." Plant Communications (2022).*
Chakraborty et al. "Evolving and assembling to pierce through: Evolutionary and structural aspects of antimicrobial peptides." Computational and Structural Biotechnology. 2022 (20): 2247-2258.*
Hu et al. "Heat shock proteins: Biological functions, pathological roles, and therapeutic opportunities." MedComm. 2022; 3 (3): e161.*
Guarra et al. "Computational Methods in Immunology and Vaccinology: Design and Development of Antibodies and Immunogens." Journal of Chemical Theory and Computation. 2023; 19 (16): 5315-5333.*
Weigand et al. "Complete genome sequences of four Bordetella pertussis vaccine reference strains from Serum Institute of India." Genome Announcements. 2016; 4 (6): 1-2.*
Lal et al. "Stability of live attenuated rotavirus vaccine with selected preservatives and primary containers." Vaccine. 2016; 34 (22): 2483-2489.*
Kutub Mahmood et al: "Hexavalent IPV-based combination vaccines for public-sector markets of low-resource countries", Human Vaccines and Immunotherapeutics, vol. 9, No. 9, Sep. 19, 2013, pp. 1894-1902.

(Continued)

*Primary Examiner* — Shanon A. Foley
(74) *Attorney, Agent, or Firm* — BakerHostetler

(57) ABSTRACT

The present disclosure relates to a fully liquid immunogenic composition comprising a combination of antigens/immunogens. The immunogenic composition comprises optimum amount of antigens/immunogens to confer protection against a number of diseases. The composition exhibits improved immunogenicity and stability. A process for preparing the vaccine composition is also disclosed.

12 Claims, No Drawings

(56) References Cited

OTHER PUBLICATIONS

Brickley Elizabeth B et al: "Maximising the impact of inactivated polio vaccines", Lancet Infectious Diseases, Elsevier Ltd, US, vol. 17, No. 7, Apr. 25, 2017, pp. 680-681.
Marta C Nunes et al: "Review of a new fully liquid, hexavalent vaccine: Hexaxim", Expert Opinion on Biological Therapy, vol. 13, No. 4, Feb. 27, 2013, pp. 575-593.

* cited by examiner

COMBINATION VACCINE COMPOSITION COMPRISING REDUCED DOSE INACTIVATED POLIOVIRUS AND METHOD FOR PREPARING THE SAME

CROSS-REFERENCE TO RELATED APPLICATIONS

The instant National Stage application claims priority to PCT/IN2019/050737 filed Oct. 4, 2019, which claims priority of Indian patent application Ser. No. 201821038850 filed Oct. 12, 2018, the contents of both which are incorporated herein in their entireties.

TECHNICAL FIELD

The present disclosure relates to the field of biotechnology, more particularly, it relates to a method of preparing the multiple-dose combination vaccine composition comprising of a group of antigens/immunogens and preservative. The present disclosure further relates to an improved methodology in the field of combination vaccine production.

BACKGROUND

A combination vaccine which can provide immunogenicity against a large number of diseases is always advantageous over the monovalent vaccine since it reduces the number of shots given, reduces complications associated with multiple intramuscular injections, reduces the administration and production costs, decreases costs of stocking, reduces risk of delayed or missed vaccinations and improves the patient compliance by reducing the number of separate vaccinations. Moreover, the fully liquid preparations of combination vaccine have distinct advantages over those which require reconstitution. Average preparation time is found to be almost half for the fully-liquid vaccine compared the non-fully-liquid vaccine. Almost all health care personnel (97.6%) stated that they would prefer the use of the fully-liquid vaccine in their daily practice. (Ref: Soubeyrand B, et al; Assessment of preparation time with fully-liquid versus non-fully liquid paediatric hexavalent vaccines. A time and motion study; Vaccine 2015; 33:3976-82).

The currently known and available combination vaccines may not contain appropriate formulations of appropriate antigens in appropriate immunogenic forms for achieving desired levels of safety, efficacy and immunogenicity in the susceptible human population for a number of diseases in one shot. The number of different vaccine combinations that can be created with just a few additional antigens is considerable. By adding 1 to 4 other antigen components (e.g. HIB (freeze-dried or liquid), HBV, IPV, HAV) to either DTwP or DTaP, there are 44 possible different vaccine combinations that can be generated. The number would increase to thousands if individual components from different manufacturers were considered. As every individual new combined vaccine (taking into account differences in components according to source) must be developed separately to demonstrate safety, stability, compatibility and efficacy the development of all these vaccines becomes a challenging task.

Antigens of the Combination Vaccine:
Diphtheria and Tetanus Antigens

Diphtheria and tetanus are acute infections caused by *Corynebacterium diphtheriae* and *Clostridium tetani*, respectively. In both instances it is a potent exotoxin of these bacteria's that is responsible for clinical disease. The vaccines affording protection against these bacteria contain toxins which are chemically modified to form toxoids a chemically modified toxin which is no longer toxic but is still antigenic. Diphtheria and Tetanus toxin are produced by growing *Corynebacterium diphtheriae* and *Clostridium tetani*, in a medium containing bovine extract. The toxins are inactivated using following treatment that include Heat, UV, Formalin/Formaldehyde, glutaraldehyde, Acetylethyleneimine, etc. for making toxoids [Diphtheria toxoid (D) and Tetanus toxoid (T)]. Concerns with respect to Bovine spongiform encephalopathy (BSE), Transmissible spongiform encephalopathy (TSE), Creutzfeldt-Jakob disease (CJD and variant CJD diseases) may arise from animal components used in the growth medium containing bovine extract spreading through the vaccine. (Ref: WHO Guidelines on Transmissible Spongiform Encephalopathies in relation to Biological and Pharmaceutical Products; 2003 & EMEA/CPMP/BWP/819/01; 24 Apr. 2001).

Pertussis Antigens

The introduction of whole-cell vaccines composed of chemically- and heat-inactivated *Bordetella pertussis* organisms in the 1940's was responsible for a dramatic reduction in the incidence of whooping cough caused by *B. pertussis*.

Whole-cell DTP vaccines are commonly associated with several local adverse events (e.g., erythema, swelling, and pain at the injection site), fever, and other mild systemic events (e.g., drowsiness, fretfulness, and anorexia) (Ref: Cody C L, Baraff L J, Cherry J D, Marcy S M, Manclarck C R; The nature and rate of adverse reactions associated with DTP and DT immunization in infants and children. Paediatrics 1981; 68:650-60) & (Ref: Long S S, DeForest A, Pennridge Pediatric Associates, et al. Longitudinal study of adverse reactions following Diphtheria-tetanus-pertussis vaccine in infancy. Paediatrics 1990; 85:294-302).

More severe systemic events (e.g., convulsions {with or without fever} and hypotonic hyporesponsive episodes) occur less frequently (ratio of one case to 1,750 doses administered) among children who receive whole-cell DTP vaccine (Ref: Cody C L, Baraff L J, Cherry J D, Marcy S M, Manclarck C R; The nature and rate of adverse reactions associated with DTP and DT immunization in infants and children. Paediatrics 1981; 68:650-60). Acute encephalopathy occurs even more rarely (ratio of 0-10.5 cases to one million doses administered). Experts do agree that whole-cell pertussis vaccine causes lasting brain damage in some rare cases. (Ref: Institute of Medicine; DPT vaccine and chronic nervous system dysfunction, a new analysis; Washington D.C., National Academy Press, 1994).

Several reports citing a relationship between whole-cell pertussis vaccination, reactogenicity and serious side-effects led to a decline in vaccine acceptance and consequent renewed epidemics (Miller, D. L., Ross, E. M., Alderslade, R., Bellman, M. H., and Brawson, N. S. B. (1981). Pertussis immunization and serious acute neurological illness in children: Brit Med. J. 282: 1595-1599).

Whole cell pertussis (wP) related adverse reactions are a hindrance for their continued use worldwide and therefore wP based combination vaccines were gradually replaced by acellular pertussis based combination vaccines in the industrialized world.

More recently, defined component pertussis vaccines have been developed. All liquid hexavalent acellular pertussis based vaccines (DTaP IPV PRP-T-HBsAg) have been previously reported (EP1028750).

Infanrix® Hexa (GSK) is presently the only globally marketed Hexavalent pediatric combination vaccine containing Salk IPV. This product (DTaP3-IPV-HBV//Hib) is sold as a prefilled syringe of the pentavalent product co-packaged with a lyophilized Hib antigen PRP-T conjugate in a separate vial to be reconstituted with the rest of the vaccine before use.

A second Hexavalent vaccine, Hexyon® (also called Hexacima® and Hexaxim®) is an all-liquid Hexavalent from Sanofi Pasteur; however it is also with aP. This vaccine is likely to be targeted for private markets in Europe and worldwide.

A heptavalent combination vaccine is being developed by Bharat Biotech International that consists of DT, Acellular pertussis, Sabin IPV (type I: 40 DU, Type 2:8 DU, Type 3:32DU), Single strain inactivated Rotavirus (G9 strain i.e 116E strain), a conjugate *Haemophilus influenza* type b PRP conjugate to TT and a Recombinant Hepatitis B vaccine.

However there have been emerging concerns about the long-term effectiveness of acellular pertussis (aP) vaccines, especially in developing-country settings. Recent reports suggest that immunity to pertussis wanes in adolescence and that this is responsible for an increase in cases in infants under six months of age, before they are fully vaccinated. Vaccine efficacy was estimated to be 24 percent in 8 to 12 year old immunized in infancy with aP. An observational study in Australia also showed higher case rates among adolescents given aP vaccine in infancy than among those given wP vaccine (relative risk of 3.3, 95 percent confidence interval 2.4-4.5).

From a cost perspective, aP antigens have historically exceeded the cost of wP antigens by a factor of 10 to 30 due to manufacturing differences and royalty costs and hence constitute an economic burden to developing countries. As a result, the cost of wP-based Hexavalent vaccines would be better suited for use in the public sector of low-resource countries.

Hence, the use of Whole cell pertussis (wP) in Hexavalent vaccines intended for developing countries has become important because of cost and emerging concerns about the long-term effectiveness of aP vaccines, especially in developing-country settings.

Compared with the best whole-cell pertussis (wP) vaccines, aP vaccines are not as effective in mass immunization programs (Vickers et al. 2006; Cherry 2012).

Recent studies of outbreaks in highly immunized populations have shown that the duration of protection of aP vaccines is too short (Klein et al. 2012; Misegades et al. 2012), resulting in a decrease in immunity in older children and adolescents, and a corresponding increase in cases in this age group (Skowronski et al. 2002; Klein et al. 2012). This is in contrast to wP vaccines, which provide protection well into the teenaged years (Klein et al. 2012). As a result of these shortcomings, in countries that switched to the aP vaccine in the 1990s we now have a generation of children not only less well-protected against pertussis but who may also be less responsive to boosters, since the vaccine with which a child is primed may determine their immune response to later booster vaccination (Podda et al. 1995; Mascart et al. 2007; Sheridan et al. 2012; Liko, Robison and Cieslak 2013; Smits et al. 2013).

One of the most important factors that contribute to the reactogenicity of wP is the presence of lipo-oligosaccharide (LOS), the endotoxin from the bacterial outer membrane.

The inactivation of toxins in wP vaccines can be done by various methods, but no active heat labile toxin should be detectable in the final product. The whole cell pertussis (wP) bulk process for inactivation of wP toxins practiced by many manufacturers use heat treatment/formalin. Several reports cite use of Thimerosal for inactivation of wP. However, use of Thimerosal causes loss of antigenicity of IPV (Vaccine 1994 Volume 12 No. 9 851-856. Deleterious effect of thimerosal on the potency of inactivated poliovirus vaccine), and therefore in case of a combination vaccine containing IPV, may need to be presented in a separate vial from thimerosal-containing wP to retain its potency over time or changing the source pertussis bulk inactivation. Some antigens i.e. active PT may also serve as immune response modifiers, and significant differences in immune responses to various antigens between different vaccines have been observed (WHO, 1993).

Chemical extraction of LOS resulted in a significant decrease in endotoxin content (20%) and a striking decline in endotoxin related toxicity (up to 97%), depending on the used in vitro or in vivo test. The LOS extraction did not affect the integrity of the product and, more importantly, did not affect the potency and/or stability of DTP. Moreover, hardly any differences in antibody and T-cell responses were observed. (Ref: Waldely Oliveira Dias et. al; An improved whole cell pertussis vaccine with reduced content of endotoxin; Human Vaccines & Immunotherapeutics 9:2, 339-348; February 2012)

Hepatitis B Antigens

There are various strains of Hepatitis virus. Hepatitis B is a disease caused by hepatitis B virus (HepB) which infects the liver of humans, and causes an inflammation called hepatitis. The vaccine against the disease contains one of the viral envelope proteins, hepatitis B surface antigen (HBsAg). Vaccines which have been used for mass immunization are now available, for example the product Recombivax HBO and Comvax® by Merck, Engerix-B® and Pediarix® by Glaxo SmithKline Biologicals. Combination vaccine having Hepatitis B component was associated with both higher completion and compliance outcomes compared with HepB single-antigen vaccine. (Ref: Kurosky. et. al; Effect of Combination Vaccines on Hepatitis B Vaccine Compliance in Children in the United States; The Pediatric Infectious Disease Journal. 36(7):e189-e196, July 2017). Several references cite adsorption of Hepatitis B surface antigen onto aluminium phosphate in combination with other antigens. Hexavac® a combination vaccine that was withdrawn from the market due to low immunogenicity of the hepatitis B component. There is therefore a need for a combination vaccine composition comprising a Hepatitis B antigen with adequate or enhanced immunogenicity.

*Haemophilus influenzae* (Hib) Antigens

*Haemophilus influenzae* is a Gram-negative coccobacillus that is a normal part of upper respiratory tract flora. *Haemophilus influenzae* type b (Hib b) is a major cause of meningitis invasive blood borne infections in young children and major cause of meningitis in the first 2 years of life. Immunization against *Haemophilus influenzae* began in Canada in 1987 with a polysaccharide vaccine [polyribose ribitol phosphate (PRP)]. The polyribosylribitol phosphate (PRP) capsule of Hib is a major virulence factor for the organism. Antibody to PRP is the primary contributor to serum bactericidal activity, and increasing levels of antibody are associated with decreasing risk of invasive disease. PRP is a T-cell independent antigen and hence is characterized by a) induction of a poor antibody response in less than 18-month-old infants and children, b) a variable and quantitatively smaller antibody response than that seen with T-cell dependent antigens, c) production of a higher proportion of immunoglobulin M (IgM), and d) inability to induce a booster response.

The initial vaccines based only on the PRP component proved to be ineffective in the infants. Further efforts were directed towards the PRP conjugate vaccine, wherein the PRP is conjugated to proteins called the carrier proteins such as the outer membrane protein of *Neisseria meningitides*, Diphtheria toxoid, Tetanus toxoid and CRM 197. The inclusion of Hib-conjugate components in combination vaccines has been associated with reduced Hib immunogenicity. Furthermore, the Hib-conjugates are unstable in aqueous media and cannot survive prolonged storage in this form. Hence, the PRP polysaccharide of *Haemophilus influenzae* b (Hib) is frequently formulated as a dried solid, which is reconstituted at the time of delivery with a liquid formulation of the other antigens. For example in Infanrix® hexa (WO99/48525).

Poliomyelitis Antigen

Different Kinds of Vaccine are Available:
- A live attenuated (weakened) oral polio vaccine (OPV) developed by Dr. Albert Sabin in 1961. OPV, comprising the Sabin strains, is given orally.
- An inactivated (killed) polio vaccine (IPV) developed in 1955 by Dr. Jonas Salk. IPV, comprising the Salk strains, is given as an injection.
- Recently, the Sabin inactivated polio virus, which was prepared by inactivating the Sabin strains polio virus with formalin, has been developed for injection and also has been available in commercial products.

Both live attenuated (OPV) and inactivated (IPV) polio vaccines have been effective in controlling the polio disease worldwide. The polio vaccine may comprise the Salk or the Sabin strains.

In 1955, Dr. Jonas Salk succeeded in inactivation of the wild type polio virus, thus enabling it in an injection type formulation, and named it as the Salk strain, which includes Mahoney type 1, MEF type 2, and Saukett type 3 that have been used in the vaccine against the poliomyelitis disease. The Sabin strains include the Sabin 1 and Sabin 2 strains.

The currently acceptable standard dose of polio vaccine(s) contains 40 D antigen units of inactivated poliovirus type 1 (Mahoney), 8 D antigen units of inactivated poliovirus type 2 (MEF-I) and 32 D antigen units of inactivated poliovirus type 3 (Saukett) e.g. Infanrix-hexa® (WO99/48525).

IPV is currently available either as a non-adjuvanted stand-alone formulation, or in various combinations, including DT-IPV (with Diphtheria and tetanus toxoids) and hexavalent-IPV vaccines (additionally with pertussis, hepatitis B, *Haemophilus influenzae* b and adjuvant) e.g. Infanrix® hexa (WO99/48525).

However, when compared to OPV, the overall production cost for IPV is significantly higher. This is mainly due to requirements for: (i) more virus per dose; (ii) additional downstream processing (i.e. concentration, purification and inactivation), and the related QC-testing (iii) loss of antigen or poor recovery in downstream and iv) containment. Until now, the financial challenge has been a major drawback for IPV innovation and implementation in low and middle-income countries.

The future global demand for IPV following eradication of polioviruses could increase from the current level of 80 million doses to 450 million doses per year. Consequently, approaches to "stretch" supplies of IPV are likely to be required.

The present applicants have surprisingly found that a reduced dose of IPV shows non-inferiority/equivalent protection against polio when compared to a standard dose of IPV antigen. Reduced-dose efficacious vaccine formulations which provide protection against infection using a lower dose of IPV antigen are desirable in situations where the supply of conventional vaccine is insufficient to meet global needs or where the cost of manufacture of the conventional vaccine prevents the vaccine being sold at a price which is affordable for developing countries. Also the exposure to lower dose of IPV; compared to the existing marketed formulations could be safer. Thus various strategies to make IPV available at more affordable prices need to be evaluated. Consequently a combination vaccine comprising reduced dose IPV could make it further cheap and easy to administer.

In case of pandemic influenza vaccines the use of adjuvants has permitted dose reduction, increased the availability and reduced cost of the vaccine. Therefore, it has been speculated that an adjuvanted vaccine formulation of IPV would reduce cost and also increase the number of available IPV doses worldwide.

Further, Aluminum salts have been considered safe, are already being used in combination vaccines containing IPV, have the lowest development hurdles and are inexpensive to manufacture. However aluminium adjuvants are not known for permitting significant dose-reduction.

In addition, Whole cell Pertussis antigen present in Hexavalent vaccine has proven to be strong immune-stimulator. Due to immune-stimulatory effect of both Aluminium phosphate adjuvant and whole cell pertussis vaccine, we presume to get good immune response with reduced dose of IPV.

Other Antigens

The other antigens that could be included in to combination vaccine are *Haemophilus influenzae* (a, c, d, e, f serotypes and the unencapsulated strains), Hepatitis (A, C, D, E, F and G strains), *Neisseria meningitis* A, B, C, W, X, Y, influenza, Pneumococci, Streptococci, Anthrax, Dengue, Malaria, Measles, Mumps, Rubella, BCG, Japanese encephalitis, Rotavirus, smallpox, Yellow fever, Typhoid, Shingles, Varicella virus, and others.

The range and the type of antigens used in a combination vaccine depend upon the target population age to be used such as infants, toddlers, children, adolescents, and adults. The earliest known combination vaccine which could prevent infection from *Bordetella pertussis, Clostridium tetani, Corynebacterium diphtheriae,* and optionally inactivated poliovirus (IPV), and/or Hepatitis B virus, and/or *Haemophilus influenzae* type B infection are known (see for instance WO 93/24148, WO97/00697, WO2000/030678, WO2008/028956, U.S. Pat. No. 6,013,264 & WO2005089794).

However, the well documented phenomenon of the antigenic competition has complicated and hindered the development of the multivalent vaccines. This phenomenon refers to the observation that administering multiple antigens together often results in a diminished response to certain antigens relative to the immune response to these antigens when administered separately.

Meanwhile, a multiple-dose vaccine should comprise of a preservative to avoid contamination by harmful microbes. For the vaccine products exported to less-developed countries, multiple-dose vaccines containing a preservative are preferred, considering the environments of the countries where the vaccines are to be used, methods of distribution etc. Examples of the preservatives that have been used include Benzethonium chloride (Phemerol), Thiomersal, Phenol, Formaldehyde and 2-phenoxyethanol (2-PE) are known in the art. Preservatives suitable for vaccines should be environmentally safe, effective against bacteria as well as yeast and other fungi and devoid of negative impact on the immunogenic effect of the vaccine.

Thiomersal is a derivative of ethyl mercury that has been extensively used in many vaccines as a preservative. Thimerosal has been known for preventing the growth of contaminating microorganisms and maintaining sterile conditions during storage or use of vaccine products, and many combination vaccines, which have acquired the WHO Prequalification (PQ), contain thimerosal as a preservative. However, there are reports pertaining to certain allergic reactions (in about 16% of population) to thiomersal primarily in the form of delayed-type local hypersensitivity reactions, including redness and swelling at the injection site.

Further, Inactivated polio vaccine conventionally uses 2-PE as a preservative instead of thiomersal since the use of thiomersal as preservative in inactivated polio vaccine is known to reduce the vaccine potency by 50% or more within a week even when stored in a refrigerator. (Vaccine 1994 Volume 12 No.9 851-856. Deleterious effect of thimerosal on the potency of inactivated poliovirus vaccine).

The combination vaccines (including D, T, wP, Hib, HBsAg, and IPV)also use 2-PE in a concentration of 5 mg/mL (WO2010046934, WO2008020322, and WO2012093406).

However, 2-PE has been found to have weaker antimicrobial activity than thimerosal against yeast and fungi in DPT based combination vaccine at 2-8° C. Improving the preservative efficacy of the combination vaccine by increasing the amount of 2-PE in order to meet the required criteria is one of the option. However, increasing the 2PE concentration may cause safety problems in young children who are the subjects to receive the combination vaccines and thereby lead to regulatory hurdles for approval of such vaccine(s).

Hence, it would be advantageous to improve the preservative efficacy of the combination vaccine by combining the 2-PE with at least one other preservative that meets the safety and regulatory criteria. Examples of the preservatives other than 2-PE that could be used include Benzethonium chloride (Phemerol), paraben esters, Phenol, formaldehyde are known in the art.

Methyl and propyl parabens, benzyl alcohol were found to pass antimicrobial testing according to USP, BP, and EP. Further these preservatives are non-toxic, yet effective. Toxicity of the parabens is relatively low, due to the ease and rapidity with which the body rids itself of these drugs. The LD50 of methyl paraben in mice intraperitoneally is 1 g/kg. A mixture of methyl and propyl parabens has never been found to be used in commercial vaccines.

The present applicants have found that the preservative efficacy of a mixture of 2-phenoxyethanol and paraben esters, (e.g. methyl-, propyl-parabens) is relatively more effective as compared to 2-phenoxyethanol alone.

Further the present applicants have found that the immunogenicity, reactogenicity, stability and the maintenance of the right form of the antigens in a combination vaccine composition depends on the way the composition has been formulated that include:
a) Process of making individual antigens
b) Sequence of addition of the antigens
c) Use of the specific adjuvants in a specific quantity for certain antigens,
d) Individual adsorption or combined adsorption of antigens onto adjuvants wherein combined adsorption has its advantages in the form of ease of operation and disadvantages include wherein the first pre-adsorbed antigens may desorb partly or completely during the addition of subsequent antigens. Antigens added at last step may not be adsorbed completely as previous antigens might saturate the adsorption capacity. Weakly adsorbed antigens might get desorbed upon storage.
e) Degree of adsorption of antigen onto adjuvants
f) using minimum Alum concentration
g) using optimal concentration and type of preservative
h) use of various parameters including agitation, temperature and pH.

Objects

Some of the objects of the present disclosure, which at least one embodiment herein satisfies, are as follows:

An object of the present disclosure is to ameliorate one or more problems of the prior art or to at least provide a useful alternative.

Another object of the present disclosure is to provide a fully liquid combination vaccine suitable for prevention and prophylaxis of infections caused by diphtheria, tetanus, pertussis, polio, *Haemophilus influenzae* and Hepatitis B or to prevent, ameliorate, or delay the onset or progression of the clinical manifestations thereof.

Yet another object of the present disclosure is to provide a fully liquid combination vaccine containing various reduced-dose Inactivated Polio Virus (IPV) antigens which shows non-inferiority/equivalent protection against polio when compared to a standard dose of IPV antigen.

Yet another object of the present disclosure is to provide a fully liquid combination vaccine containing at least one paraben i.e. methyl or propyl paraben preservative and 2-phenoxyethanol (2-PE) to improve the preservative efficacy of the multi-dose combination vaccine.

Yet another object of the present disclosure is to provide an improved method of manufacturing such composition/formulation of the combination vaccine wherein, the vaccine showing improved immunogenicity reduced reactogenicity, improved stability and further meets the criterion for the seroprotection for each of the said immunogenic components.

Other objects and advantages of the present disclosure will be more apparent from the following description, which is not intended to limit the scope of the present disclosure.

SUMMARY OF INVENTION

A combination vaccine composition comprising of reduced-dose Inactivated Polio Virus (IPV) antigen combined with other antigens/immunogens and at least one paraben esters i.e. methyl or propyl paraben and 2-phenoxyethanol(2-PE) used as preservative wherein the preservative efficacy of the multi-dose combination vaccine is improved and process of making thereof.

The present disclosure relates to a combination vaccine composition comprising of
a) A highly purified Diphtheria toxoid (D) & tetanus toxoid (T) produced using semi synthetic medium, subsequently detoxified and individually adsorbed onto aluminium phosphate adjuvant thereby resulting in enhanced immunogenicity
b) Inactivated whole-cell *B. pertussis* (wP) component prepared using a combination of heat and chemical inactivation, specific *Bordetella pertussis* strains in a particular ratio resulting in reduced reactogenicity and increased potency.
c) *Haemophilus influenzae* type b (Hib) capsular polysaccharide antigen (PRP) conjugated to a carrier protein (CP)
d) Reduced dose of Salk or Sabin (Inactivated Polio Virus) IPV showing comparable efficacy as compared to standard dose prepared by utilizing improved methods of formaldehyde inactivation and optionally adsorbing onto aluminium phosphate adjuvant.

e) Hepatitis B (HepB) surface antigen adsorbed individually onto aluminium phosphate adjuvant thereby resulting in enhanced immunogenicity f) Minimum alum content thereby ensuring reduced reactogenicity g) At least one paraben esters i.e. methyl or propyl paraben other than 2-phenoxyethanol (2-PE) as preservative.

DETAILED DESCRIPTION

Although the present disclosure may be susceptible to different embodiments, certain embodiments are shown in the following detailed discussion, with the understanding that the present disclosure can be considered an exemplification of the principles of the disclosure and is not intended to limit the scope of disclosure to that which is illustrated and disclosed in this description. Embodiments are provided so as to thoroughly and fully convey the scope of the present disclosure to the person skilled in the art. Numerous details are set forth, relating to specific components, and methods, to provide a complete understanding of embodiments of the present disclosure. It will be apparent to the person skilled in the art that the details provided in the embodiments should not be construed to limit the scope of the present disclosure. In some embodiments, well-known composition, well-known processes, and well-known techniques are not described in detail.

The terminology used, in the present disclosure, is only for the purpose of explaining a particular embodiment and such terminology shall not be considered to limit the scope of the present disclosure. As used in the present disclosure, the forms "a," "an," and "the" may be intended to include the plural forms as well, unless the context clearly suggests otherwise.

The terms first, second, third, etc., should not be construed to limit the scope of the present disclosure as the aforementioned terms may be only used to distinguish one element, component, region, layer or section from another component, region, layer or section. Terms such as first, second, third etc., when used herein do not imply a specific sequence or order unless clearly suggested by the present disclosure. The present disclosure provides an immunogenic composition and a process for preparing the same.

The term "vaccine" is optionally substitutable with the term "immunogenic composition" and vice versa.

"D-antigen units" (also referred to as "international units" or IU): The D antigenic form of the poliovirus induces protective neutralising antibodies. D antigen units referred to herein (for instance in the vaccines of the invention) are the measured total D antigen units of each unadsorbed bulk IPV antigen type prior to formulation of the final vaccine which are added in each human dose of formulated vaccine (typically 0.5 mL final volume). Reliable methods of measuring D-antigen units are well known in the art and are published, for instance, by the European Pharmacopoeia. For instance, D-antigen units may be measured using the ELISA test as described in Example 1 ("D-antigen quantification by ELISA") below. European Pharmacopoeia provides a test sample (European Pharmacopoeia Biological Reference Preparation—available from Ph. Eur. Secretariat, e.g. Code P 216 0000) for standardisation of such methods between manufacturers (Pharmeuropa Special Issue, Bio 96-2). Thus the D-antigen unit value is well understood in the art.

The term "dose" herein is typically one administration of the vaccine of the invention, which is typically one injection.

A typical human dose is 0.5 mL. Of course various doses may be administered in a vaccine administration schedule.

The term "IPV" or a immunogenic composition comprising these components herein is intended to mean inactivated polio virus type 1 (e.g. Mahoney, as preferably used), type 2 (e.g. MEF-1), or type 3 (e.g. Saukett), or a Sabin Serotype 1, 2, 3 combination of either two or all three of these types. An example of a full (or standard) dose (40-8-32 D antigen units of Salk based IPV types 1, 2 and 3 respectively) IPV immunogenic composition for the purposes of this invention could be Poliovac® (Serum Institute of India Pvt. Ltd.). Thus, where it is stated herein that one, two, three fold dose reduction (reduced)as compared to standard dose of Salk based IPV is present in an immunogenic composition of the invention it is meant D-antigen units equating to X % of reduction of dose of 40, 8, and/or 32 D-antigen units of IPV types 1, 2 and/or 3 respectively (as measured in each bulk IPV antigen type) are formulated within each dose of said vaccine.

The term "saccharide" throughout this specification may indicate polysaccharide or oligosaccharide and includes both. The capsular saccharide antigen may be a full length polysaccharide or it may be extended to bacterial 'sized-saccharides' and 'oligosaccharides' (which naturally have a low number of repeat units, or which are polysaccharides reduced in size for manageability, but are still capable of inducing a protective immune response in a host.

According to a first embodiment of the present disclosure, the combination vaccine composition comprise of a group of antigens/immunogens selected from but not limited to Diphtheria toxoid (D), Tetanus toxoid (T), Whole cell *B. pertussis* (wP), *Haemophilus influenzae* type b (Hib) PRP-CP conjugate, Hepatitis B (HepB), reduced dose of Inactivated Polio Virus (IPV) and additionally comprise of a combination of 2-phenoxyethanol and at least one paraben ester preservatives.

According to a second embodiment of the present disclosure, the combination vaccine composition could further comprise of one or more antigens selected from the group consisting of but not limited to *Haemophilus influenzae*(a, c, d, e, f serotypes and the unencapsulated strains), Hepatitis (A, C, D, E, F and G strains), *Neisseria meningitidis* A, B, C, Y, W-135, or X, influenza, *Staphylococcus aureus*, *Salmonella typhi* antigen(s), acellular pertussis antigen, modified adenylate cyclase, Malaria Antigen (RTS,S), *Pneumococci, Streptococci*, anthrax, dengue, malaria, measles, mumps, rubella, BCG, Human papilloma virus, Japanese encephalitis, Dengue, Zika, Ebola, Chikungunya, Rotavirus, smallpox, yellow fever, Flavivirus, Shingles, Varicella virus antigens respectively.

According to a third embodiment of the present disclosure, the IPV strains used in the combination vaccine composition comprise of inactivated Sabin strains selected from the group of type 1, type 2, and type 3 or inactivated Salk strains selected from the group of Mahoney type 1, MEF type 2 and Saukett type 3.

In one of the aspects of the third embodiment, Polio virus may be grown by following method:

CCL81-VERO (Monkey kidney) cell line was used as host cells for the growing of polio viruses i.e. Sabin and Salk strains.

After infection of host cells with desired strain of polio virus and incubation of 72 hours, the medium containing the virus and cell debris was pooled and collected in a single container.

The filtrate was subjected to tangential flow filtration with 100 KDa cassette; diafiltered using phosphate buffer and purified using anion exchange chromatography.

Prior to administration to patients, the viruses must be inactivated using appropriate inactivation methods.

However, the present inventors have surprisingly found that the high percentage loss of D-antigen post-formaldehyde inactivation could be due to presence of phosphate buffer that unexpectedly causes undesirable aggregation of polio virus particles.

Hence, an important aspect of the present disclosure comprise of, an improved process of formalin inactivation comprising of following steps:

a) The purified virus pool was subjected to buffer exchange from Phosphate buffer to Tris buffer in the range of (30 to 50 mM) having pH between 7 to 7.5, b) To the above mixture M-199 medium containing glycine (5 gm/l) was added c) 0.025% formaldehyde was added and subsequently mixed, d) The mixture was subsequently incubated at 37° C. for 5 to 13 days with continuous stirring of virus bulk on magnetic stirrer, e) The post-incubation mixture was subjected to intermediate TFF system (100 KDa, 0.1 m$^2$) on day 7 and final filtration after inactivation f) Subsequently the filtered bulk was stored at 2-8° C., g) Performing D-Ag ELISA for D-Ag unit determination According to a fourth embodiment of the present disclosure, the IPV strains used in the combination vaccine composition comprise of dose reduced inactivated Sabin strains selected from the group of type 1, type 2, and type 3 or inactivated Salk strains selected from the group of Mahoney type 1, MEF type 2 and Saukett type 3.

According to a fifth embodiment of the present disclosure, the IPV (Sabin or Salk Strains) may not be adsorbed individually onto any adjuvant and subsequently added to the final combination vaccine composition.

According to a preferred aspect of fifth embodiment, the IPV (Sabin or Salk Strains) may be adsorbed on the adjuvant more preferably aluminium salt of phosphate or hydroxide present in the combination vaccine wherein the percentage adsorption of IPV antigen for IPV type 1 may be in the range of 10-30%, IPV type 2 may be in the range of 60-100% and IPV type 3 may be in the range of 0-25%.

According to a sixth embodiment of the present disclosure, the IPV (Sabin or Salk Strains) component(s) may be individually adsorbed onto an adjuvant selected from the group of aluminium salt ($Al^{3+}$) such as aluminium hydroxide ($Al(OH)_3$) or aluminium phosphate ($AlPO_4$), alum, calcium phosphate, MPLA, 3D-MPL, QS21, a CpG-containing oligodeoxynucleotide adjuvant, liposome, or oil-in-water emulsion or a combination thereof. (e.g. before or after mixing with other components if present). If adsorbed, one or more IPV components may be adsorbed separately or together as a mixture on aluminium hydroxide ($Al(OH)_3$) or aluminium phosphate.

The IPV (Sabin or Salk Strains) component(s) may be adsorbed onto an aluminium salt by following procedure:

Taking the desired volume of autoclaved $Al(PO)_4$ or $Al(OH)_3$ to get the final Alum ($Al^{3+}$) concentration between 0.1 to 0.8 mg/dose in a 50 ml container Adding IPV bulk with adjusted D-Ag unit and making up the volume with diluent (10×M-199+0.5% Glycine), Adjusting the final formulation pH and obtaining final formulation with pH between 6 and 7.5.

In one of the aspect of the sixth embodiment, adsorption of formalin inactivated IPV can be done on Alum ($Al^{3+}$) having concentration selected from 0.1 mg/dose, 0.2 mg/dose, 0.3 mg/dose, 0.4 mg/dose, 0.5 mg/dose, 0.6 mg/dose, 0.7 mg/dose and 0.8 mg/dose, preferably between 0.1 mg/dose to 1.25 mg/dose per serotype and at a pH selected from 6.2, 6.3, 6.4, 6.5, 6.6, 6.7 and 6.8 preferably 6.5.

In a yet another aspect of the sixth embodiment, the percent recovery of D-Antigen post formalin inactivation in presence of Tris could be either 50%,60%,70% or 80% and percent adsorption post aluminium phosphate adsorption could be between 70% to 80%,80% to 90% or 90% to 99% or 95% to 99%.

According to a seventh embodiment of the present disclosure, Diphtheria toxin (exotoxin) and tetanus toxin (exotoxin) were obtained from *Corynebacterium Diphtheria* and *Clostridium tetani* respectively and subsequently detoxified using a suitable inactivation method. The Diphtheria toxoid (D) and Tetanus toxoid (T) thus obtained may be purified using Gel filtration chromatography. The purified DT thus obtained was further used for formulation of combination vaccine.

In one of the aspect of the seventh embodiment, Diphtheria toxin is produced by growing *Corynebacterium diphtheriae* in a semi synthetic medium consisting of following ingredients at optimal concentrations in any one of the following combinations:

Combination 1:

Casein Hydrolysate, Maltose Monohydrate, Glacial Acetic acid, Sodium lactate, Magnesium Sulphate, β-alanine, Pimelic acid, Nicotinic acid, Cupric Sulphate, Zinc Sulphate, Manganous Chloride, L-Cystine, Calcium Chloride Dihydrate, Potassium Dihydrogen Orthophosphate, Di Potassium Hydrogen Phosphate, Ferrous Sulphate and WFI.

Combination 2:

Casein Hydrolysate, Maltose Monohydrate, Glacial Acetic acid, Sodium lactate, Magnesium Sulphate, β-alanine, Pimelic acid, Nicotinic acid, Manganous Chloride, L-Cystine, Calcium Chloride Dihydrate, Potassium Dihydrogen Orthophosphate, Di Potassium Hydrogen Phosphate, Ferrous Sulphate and WFI.

Combination 3:

Casein Hydrolysate, Maltose Monohydrate, Glacial Acetic acid, Sodium lactate, β-alanine, Pimelic acid, Nicotinic acid, Cupric Sulphate, Zinc Sulphate, Manganous Chloride, L-Cystine, Calcium Chloride Dihydrate, Potassium Dihydrogen Orthophosphate, Di Potassium Hydrogen Phosphate, and WFI.

Combination 4:

Yeast extract, Maltose Monohydrate, Glacial Acetic acid, Sodium lactate, Magnesium Sulphate, β-alanine, Pimelic acid, Nicotinic acid, Cupric Sulphate, Zinc Sulphate, Manganous Chloride, L-Cystine, Calcium Chloride Dihydrate, Potassium Dihydrogen Orthophosphate, Di Potassium Hydrogen Phosphate, Ferrous Sulphate and WFI.

According to second aspect of the seventh embodiment, Tetanus toxin is produced by growing *Clostridium tetanus* in a semi synthetic medium consisting of following ingredients at optimal concentrations in any one of the following combinations:

Combination 1:

Casein Digest, Calcium Chloride, Di Potassium Hydrogen Phosphate, Anhydrous Dextrose, Sodium chloride, Magnesium sulfate, Riboflavin, Thiamine hydrochloride, Pyridoxine hydrochloride, Calcium pantothenate, Nicotinic acid, L-Cystine, Ferric chloride, Vitamin B12 solution, Biotin, Conc. HCl, NaOH, Absolute Ethanol, and WFI Combination 2:

Casein Digest, Calcium Chloride, β-alanine Di Potassium Hydrogen Phosphate, Anhydrous Dextrose, Sodium chloride, Magnesium sulfate, Ferrous Sulphate, Riboflavin, Thiamine hydrochloride, Pyridoxine hydrochloride, Calcium pantothenate, Nicotinic acid, L-Cystine, Ferric chloride, Vitamin B12 solution, Biotin, Conc. HCl, NaOH, Absolute Ethanol, and WFI Combination 3:

Casein Digest, Calcium Chloride, Di Potassium Hydrogen Phosphate, Anhydrous Dextrose, Sodium chloride, Zinc Sulphate, Riboflavin, Thiamine hydrochloride, Pyridoxine hydrochloride, Calcium pantothenate, Nicotinic acid, L-Cystine, Ferric chloride, Vitamin B12 solution, Biotin, Conc. HCl, NaOH, Absolute Ethanol, and WFI Combination 4:

Casein hydrolysate, Calcium Chloride, Di Potassium Hydrogen Phosphate, Anhydrous Dextrose, Sodium chloride, Magnesium sulfate, Manganous Chloride Riboflavin, Thiamine hydrochloride, Pyridoxine hydrochloride, Calcium pantothenate, Nicotinic acid, L-Cystine, Ferric chloride, Vitamin B12 solution, Biotin, Conc. HCl, NaOH, Absolute Ethanol, and WFI In a yet another aspect of the seventh embodiment, the Diphtheria and tetanus toxin was detoxified using one or combination of following inactivation methods that include Heat, UV, Formalin/Formaldehyde, Acetylethyleneimine, etc.

According to an eighth embodiment of the present disclosure, the Hepatitis (Hep) antigen used in the combination vaccine composition comprise of Hepatitis antigens derived from the surface of Hepatitis B strain (HBsAg).

In one of the aspect of the ninth embodiment, HBsAg can be made by one of the following methods:

By purifying the antigen in particulate form from the plasma of chronic hepatitis B carriers, as large quantities of HBsAg are synthesized in the liver and released into the blood stream during an HBV infection Expressing the protein by recombinant DNA methods According to a ninth embodiment of the present disclosure, Diphtheria toxoid (D), Tetanus toxoid (T), Hepatitis B surface antigen (HBsAg) are individually adsorbed on to adjuvant selected from the group of aluminium salt ($Al^{3+}$) such as aluminium hydroxide ($Al(OH)_3$) or aluminium phosphate ($AlPO_4$), alum, calcium phosphate, MPLA, 3D-MPL, QS21, a CpG-containing oligodeoxynucleotide adjuvant, liposome, or oil-in-water emulsion or a combination thereof.

Yet preferably Diphtheria toxoid (D), Tetanus toxoid (T) and Hepatitis B surface antigen (HBsAg) are individually adsorbed on to aluminium phosphate.

In one of the aspect of the ninth embodiment, the Diphtheria toxoid (D) antigen adsorbed on to aluminium phosphate having percentage adsorption of at least 50%.

In another aspect of the ninth embodiment, the tetanus toxoid (T) antigen adsorbed on to aluminium phosphate having percentage adsorption of at least 40%.

In a yet another aspect of the ninth embodiment, the Hepatitis B surface antigen (HBsAg) adsorbed on to aluminium phosphate having percentage adsorption of at least 70%.

According to a tenth embodiment of the present disclosure, the Hib antigen used in the combination vaccine of the present disclosure is derived from the capsular polysaccharide of *Haemophilus influenzae* type B (Hib) strain 760705.

According to one aspect of the tenth embodiment, the Hib PRP antigen is conjugated to a carrier protein selected from a group of carrier protein consisting of but not limited to CRM197, Diphtheria toxoid, *Neisseria meningitidis* outer membrane complex, fragment C of tetanus toxoid, pertussis toxoid, protein D of *H. influenzae*, *E. coli* LT, *E. coli* ST, and exotoxin A from *Pseudomonas aeruginosa*, outer membrane complex c (OMPC), porins, transferrin binding proteins, pneumolysin, pneumococcal surface protein A (PspA), pneumococcal surface adhesin A (PsaA), pneumococcal PhtD, pneumococcal surface proteins BVH-3 and BVH-11, protective antigen (PA) of *Bacillus anthracis* and detoxified edema factor (EF) and lethal factor (LF) of *Bacillus anthracis*, ovalbumin, keyhole limpet hemocyanin (KLH), human serum albumin, bovine serum albumin (BSA) and purified protein derivative of tuberculin (PPD), synthetic peptides, heat shock proteins, pertussis proteins, cytokines, lymphokines, hormones, growth factors, artificial proteins comprising multiple human CD4+ T cell epitopes from various pathogen-derived antigens such as N 19, iron-uptake proteins, toxin A or B from *C. difficile* and *S. agalactiae* proteins.

Yet preferably the Hib PRP is conjugated to tetanus toxoid (TT). by CNBr chemistry, Reductive amination chemistry, Cyanylation chemistry or any other chemistry already discloses in Kniskern et al., "Conjugation: design, chemistry, and analysis" in Ellis et al., Development and clinical uses of *Haemophilus influenzae* type B conjugate vaccines. New York: Marcel Dekker, 1994: 37-69

According to second aspect of the tenth embodiment, the carrier protein is present in both free and conjugated form in a composition of the present disclosure, the unconjugated form is preferably no more than 20% of the total amount of the carrier protein in the composition as a whole, and more preferably present at less than 5% by weight.

According to third aspect of the tenth embodiment, the Hib antigen is not substantially adsorbed on to any adjuvant.

According to fourth aspect of the tenth embodiment, the Hib antigen may not be subjected to deliberate or intentional adsorption on any adjuvant.

According to fifth aspect of the tenth embodiment, the percentage of adsorption of Hib antigen on to any adjuvant is less than 20%.

According to an eleventh embodiment of the present disclosure, whole cell pertussis (wP) antigen preparation used in the combination vaccine composition of the present disclosure is preferably made from *Bordetella pertussis* strains 134, 509, 25525 and 6229 mixed in a specific ratio and subsequently inactivated by utilizing improved methods of inactivation devoid of thiomersal hence leading to reduced reactogenicity & increased potency and wP antigen may or may not be adsorbed onto aluminium based adjuvants.

According to one aspect of the eleventh embodiment, whole cell pertussis (wP) antigen preparation used in the combination vaccine composition of the present disclosure is preferably made from *Bordetella pertussis* strains 134, 509, 25525 and 6229 mixed in a ratio of 1:1:0.25:0.25.

According to second aspect of the eleventh embodiment, whole cell pertussis (wP) antigen preparation used in the combination vaccine composition was inactivated using one or more of following inactivation treatment that include Heat, UV, Formalin/Formaldehyde, Acetylethyleneimine, etc.

Yet preferably whole cell pertussis (wP) antigen preparation used in the combination vaccine composition was inactivated using a combination of heat and chemical treatment. Yet preferably heat inactivated at 56±2° C., 10 to 15 mins in presence of formaldehyde wherein, wP bulk remains non-clumpy and easily homogenized thereby leading to reduced reactogenicity and giving better wP potency for a longer duration.

According to third aspect of the eleventh embodiment, whole cell pertussis (wP) antigen preparation used in the combination vaccine composition may or may not be adsorbed onto an aluminium based adjuvant such as aluminium hydroxide, aluminium phosphate or combination thereof (e.g. before or after mixing with other components if present). If adsorbed, one or more wP strains (i.e. 134, 509, 25525 and 6229) may be adsorbed individually or together as a mixture.

According to a twelfth embodiment of the present disclosure, the multi-dose combination vaccine composition/formulation comprises of:

TABLE 1

| Sr. No. | Formulation Components | Antigen Unit/0.5 ml Dose | Preferred Antigen Unit/0.5 ml Dose (In any of the combination) |
|---|---|---|---|
| 1 | Diphtheria Toxoid (D) | 10-25 Lf | Preferably one of 10 or 20 or 25 Lf |
| 2 | Tetanus toxoid (T) | 02-10 Lf | Preferably one of 2or 4 or 10 Lf |
| 3 | Inactivated *B. pertussis* antigen (wP) | 12-16 IOU | Preferably one of 12 or 14 or 16 IOU |
| 4 | HBs antigen | 7-15 µg | Preferably one of 8 or 10 or 15 µg |
| 5 | Hib PRP-TT conjugate antigen | 7-13 µg of PRP | Preferably one of 8 or 10 or 13 µg of PRP |
| 6 | Inactivated Polio Virus (IPV) Sabin Serotype | | |
| | Type 1 (D antigen units) | 1-50 DU | Preferably one of 5 or 10 or 20 DU |
| | Type 2 (D antigen units) | 1-50 DU | Preferably one of 8 or 4 or 16 DU |
| | Type 3 (D antigen units) | 1-50 DU | Preferably one of 10 or 16 or 32 DU |
| 7 | Total Aluminium Content ($Al^{3+}$) (as Aluminium Phosphate) | 0.1-0.6 mg | Preferably NMT 0.3 or NMT 0.55 or NMT 0.63 |
| 8 | 2-Phenoxyethanol | 1-6 mg | Preferably one of 2 or 2.5 or 3 mg |
| 9 | Methylparaben | 0.1-1.5 mg | Preferably one of 0.7 or 0.9 or 1 mg |
| 10 | Propylparaben | 0.05-0.2 mg | Preferably one of 0.05 or 0.1 or 0.15 mg |

According to a thirteenth embodiment of the present disclosure, the multi-dose combination vaccine composition/formulation comprises of:

TABLE 2

| Sr. No. | Formulation Components | Antigen Unit/0.5 ml Dose | Preferred Antigen Unit/0.5 ml Dose (In any of the combination) |
|---|---|---|---|
| 1 | Diphtheria Toxoid (D) | 10-25 Lf | Preferably one of 10 or 20 or 25 Lf |
| 2 | Tetanus toxoid (T) | 02-10 Lf | Preferably one of 2or 4 or 10 Lf |
| 3 | Inactivated *B. pertussis* antigen (wP) | 12-16 IOU | Preferably one of 12 or 14 or 16 IOU |
| 4 | HBs antigen | 7-15 µg | Preferably one of 8 or 10 or 15 µg |
| 5 | Hib PRP-TT conjugate antigen | 7-13 µg of PRP | Preferably one of 8 or 10 or 13 µg of PRP |
| 6 | Inactivated Polio Virus (IPV) Salk Serotype | | |
| | Mahoney Type 1 (D antigen units) | 1-50 DU | Preferably one of 7.5 or 10 or 20 or 40 DU |
| | MEF-1 Type 2 (D antigen units) | 1-50 DU | Preferably one of 1.5 or 2 or 4 or 8 DU |
| | Saukett Type 3 (D antigen units) | 1-50 DU | Preferably one of 6 or 10 or 16 or 32 DU |
| 7 | Total Aluminium Content ($Al^{3+}$) (as Aluminium Phosphate) | 0.1-0.6 mg | Preferably NMT 0.3 or NMT 0.55 or NMT 0.63 |
| 8 | 2-Phenoxyethanol | 1-6 mg | Preferably one of 2 or 2.5 or 3 mg |
| 9 | Methylparaben | 0.1-1.5 mg | Preferably one of 0.7 or 0.9 or 1 mg |
| 10 | Propylparaben | 0.05-0.2 mg | Preferably one of 0.05 or 0.1 or 0.15 mg |

According to a fourteenth embodiment of the present disclosure, the multi-dose combination vaccine composition/formulation comprises of:

TABLE 3

| Sr. No. | Formulation Components | Antigen Unit/0.5 ml Dose | Preferred Antigen Unit/0.5 ml Dose (In any of the combination) |
|---|---|---|---|
| 1 | Diphtheria Toxoid (D) | 10-25 Lf | Preferably one of 10 or 20 or 25 Lf |
| 2 | Tetanus toxoid (T) | 02-10 Lf | Preferably one of 2or 4 or 10 Lf |

TABLE 3-continued

| Sr. No. | Formulation Components | Antigen Unit/0.5 ml Dose | Preferred Antigen Unit/0.5 ml Dose (In any of the combination) |
|---|---|---|---|
| 3 | Inactivated *B. pertussis* antigen (wP) | 12-16 IOU | Preferably one of 12 or 14 or 16 IOU |
| 4 | HBs antigen | 7-15 µg | Preferably one of 8 or 10 or 15 µg |
| 5 | Hib PRP-TT conjugate antigen | 7-13 µg of PRP | Preferably one of 8 or 10 or 13 µg of PRP |
| 6 | Inactivated Polio Virus (IPV) Sabin Serotype | | |
|   | Type 1 (D antigen units) | 1-50 DU | Preferably one of 5 or 10 or 20 DU |
|   | Type 3 (D antigen units) | 1-50 DU | Preferably one of 10 or 16 or 32 DU |
| 7 | Total Aluminium Content ($Al^{3+}$) (as Aluminium Phosphate) | 0.1-0.6 mg | Preferably NMT 0.3 or NMT 0.55 or NMT 0.63 |
| 8 | 2-Phenoxyethanol | 1-6 mg | Preferably one of 2 or 2.5 or 3 mg |
| 9 | Methylparaben | 0.1-1.5 mg | Preferably one of 0.7 or 0.9 or 1 mg |
| 10 | Propylparaben | 0.05-0.2 mg | Preferably one of 0.05 or 0.1 or 0.15 mg |

According to a fifteenth embodiment of the present disclosure, the multi-dose combination vaccine composition/formulation comprises of:

TABLE 4

| Sr. No. | Formulation Components | Antigen Unit/0.5 ml Dose | Preferred Antigen Unit/0.5 ml Dose (In any of the combination) |
|---|---|---|---|
| 1 | Diphtheria Toxoid (D) | 10-25 Lf | Preferably one of 10 or 20 or 25 Lf |
| 2 | Tetanus toxoid (T) | 02-10 Lf | Preferably one of 2 or 4 or 10 Lf |
| 3 | Inactivated *B. pertussis* antigen (wP) | 12-16 IOU | Preferably one of 12 or 14 or 16 IOU |
| 4 | HBs antigen | 7-15 µg | Preferably one of 8 or 10 or 15 µg |
| 5 | Hib PRP-TT conjugate antigen | 7-13 µg of PRP | Preferably one of 8 or 10 or 13 µg of PRP |
| 6 | Inactivated Polio Virus (IPV) Salk Serotype | | |
|   | Mahoney Type 1 (D antigen units) | 1-50 DU | Preferably one of 7.5 or 10 or 20 or 40 DU |
|   | Saukett Type 3 (D antigen units) | 1-50 DU | Preferably one of 6 or 10 or 16 or 32 DU |
| 7 | Total Aluminium Content ($Al^{3+}$) (as Aluminium Phosphate) | 0.1-0.6 mg | Preferably NMT 0.3 or NMT 0.55 or NMT 0.63 |
| 8 | 2-Phenoxyethanol | 1-6 mg | Preferably one of 2 or 2.5 or 3 mg |
| 9 | Methylparaben | 0.1-1.5 mg | Preferably one of 0.7 or 0.9 or 1 mg |
| 10 | Propylparaben | 0.05-0.2 mg | Preferably one of 0.05 or 0.1 or 0.15 mg |

According to a sixteenth embodiment of the present disclosure, the multi-dose combination vaccine composition/formulation comprises of:

TABLE 5

| Sr. No. | Formulation Components | Antigen Unit/0.5 ml Dose | Preferred Antigen Unit/0.5 ml Dose (In any of the combination) |
|---|---|---|---|
| 1 | Diphtheria Toxoid (D) | 10-25 Lf | Preferably one of 10 or 20 or 25 Lf |
| 2 | Tetanus toxoid (T) | 02-10 Lf | Preferably one of 2 or 4 or 10 Lf |
| 3 | Inactivated *B. pertussis* antigen (wP) | 12-16 IOU | Preferably one of 12 or 14 or 16 IOU |
| 4 | HBs antigen | 7-15 µg | Preferably one of 8 or 10 or 15 µg |
| 5 | Hib PRP-TT conjugate antigen | 7-13 µg of PRP | Preferably one of 8 or 10 or 13 µg of PRP |
| 6 | Inactivated Polio Virus (IPV) Sabin Serotype | | |
|   | Type 1 (D antigen units) | 1-50 DU | Preferably one of 5 or 10 or 20 DU |
|   | Type 2 (D antigen units) | 1-50 DU | Preferably one of 8 or 4 or 16 DU |
|   | Type 3 (D antigen units) | 1-50 DU | Preferably one of 10 or 16 or 32 DU |
| 7 | Total Aluminium Content ($Al^{3+}$) (as Aluminium Phosphate) | 0.1-0.6 mg | Preferably NMT 0.3 or NMT 0.55 or NMT 0.63 |
| 8 | 2-Phenoxyethanol | 1-6 mg | Preferably one of 2 or 2.5 or 3 mg |
| 9 | Methylparaben | 0.1-1.5 mg | Preferably one of 0.7 or 0.9 or 1 mg |

According to a seventeenth embodiment of the present disclosure, the multi-dose combination vaccine composition/formulation comprises of:

TABLE 6

| Sr. No. | Formulation Components | Antigen Unit/0.5 ml Dose | Preferred Antigen Unit/0.5 ml Dose (In any of the combination) |
|---|---|---|---|
| 1 | Diphtheria Toxoid (D) | 10-25 Lf | Preferably one of 10 or 20 or 25 Lf |
| 2 | Tetanus toxoid (T) | 02-10 Lf | Preferably one of 2 or 4 or 10 Lf |
| 3 | Inactivated *B. pertussis* antigen (wP) | 12-16 IOU | Preferably one of 12 or 14 or 16 IOU |
| 4 | HBs antigen | 7-15 µg | Preferably one of 8 or 10 or 15 µg |
| 5 | Hib PRP-TT conjugate antigen | 7-13 µg of PRP | Preferably one of 8 or 10 or 13 µg of PRP |
| 6 | Inactivated Polio Virus (IPV) Salk Serotype | | |
|  | Mahoney Type 1 (D antigen units) | 1-50 DU | Preferably one of 7.5 or 10 or 20 or 40 DU |
|  | MEF-1 Type 2 (D antigen units) | 1-50 DU | Preferably one of 1.5 or 2 or 4 or 8 DU |
|  | Saukett Type 3 (D antigen units) | 1-50 DU | Preferably one of 6 or 10 or 16 or 32 DU |
| 7 | Total Aluminium Content ($Al^{3+}$) (as Aluminium Phosphate) | 0.1-0.6 mg | Preferably NMT 0.3 or NMT 0.55 or NMT 0.63 |
| 8 | 2-Phenoxyethanol | 1-6 mg | Preferably one of 2 or 2.5 or 3 mg |
| 9 | Methylparaben | 0.1-1.5 mg | Preferably one of 0.7 or 0.9 or 1 mg |

According to a eighteenth embodiment of the present disclosure, the multi-dose combination vaccine composition/formulation comprises of:

TABLE 7

| Sr. No. | Formulation Components | Antigen Unit/0.5 ml Dose | Preferred Antigen Unit/0.5 ml Dose (In any of the combination) |
|---|---|---|---|
| 1 | Diphtheria Toxoid (D) | 10-25 Lf | Preferably one of 10 or 20 or 25 Lf |
| 2 | Tetanus toxoid (T) | 02-10 Lf | Preferably one of 2 or 4 or 10 Lf |
| 3 | Inactivated *B. pertussis* antigen (wP) | 12-16 IOU | Preferably one of 12 or 14 or 16 IOU |
| 4 | HBs antigen | 7-15 µg | Preferably one of 8 or 10 or 15 µg |
| 5 | Hib PRP-TT conjugate antigen | 7-13 µg of PRP | Preferably one of 8 or 10 or 13 µg of PRP |
| 6 | Inactivated Polio Virus (IPV) Sabin Serotype | | |
|  | Type 1 (D antigen units) | 1-50 DU | Preferably one of 5 or 10 or 20 DU |
|  | Type 3 (D antigen units) | 1-50 DU | Preferably one of 10 or 16 or 32 DU |
| 7 | Total Aluminium Content ($Al^{3+}$) (as Aluminium Phosphate) | 0.1-0.6 mg | Preferably NMT 0.3 or NMT 0.55 or NMT 0.63 |
| 8 | 2-Phenoxyethanol | 1-6 mg | Preferably one of 2 or 2.5 or 3 mg |
| 9 | Methylparaben | 0.1-1.5 mg | Preferably one of 0.7 or 0.9 or 1 mg |

According to a nineteenth embodiment of the present disclosure, the multi-dose combination vaccine composition/formulation comprises of:

TABLE 8

| Sr. No. | Formulation Components | Antigen Unit/0.5 ml Dose | Preferred Antigen Unit/0.5 ml Dose (In any of the combination) |
|---|---|---|---|
| 1 | Diphtheria Toxoid (D) | 10-25 Lf | Preferably one of 10 or 20 or 25 Lf |
| 2 | Tetanus toxoid (T) | 02-10 Lf | Preferably one of 2 or 4 or 10 Lf |
| 3 | Inactivated *B. pertussis* antigen (wP) | 12-16 IOU | Preferably one of 12 or 14 or 16 IOU |
| 4 | HBs antigen | 7-15 µg | Preferably one of 8 or 10 or 15 µg |
| 5 | Hib PRP-TT conjugate antigen | 7-13 µg of PRP | Preferably one of 8 or 10 or 13 µg of PRP |
| 6 | Inactivated Polio Virus (IPV) Salk Serotype | | |
|  | Mahoney Type 1 (D antigen units) | 1-50 DU | Preferably one of 7.5 or 10 or 20 or 40 DU |
|  | Saukett Type 3 (D antigen units) | 1-50 DU | Preferably one of 6 or 10 or 16 or 32 DU |

TABLE 8-continued

| Sr. No. | Formulation Components | Antigen Unit/0.5 ml Dose | Preferred Antigen Unit/0.5 ml Dose (In any of the combination) |
|---|---|---|---|
| 7 | Total Aluminium Content ($Al^{3+}$) (as Aluminium Phosphate) | 0.1-0.6 mg | Preferably NMT 0.3 or NMT 0.55 or NMT 0.63 |
| 8 | 2-Phenoxyethanol | 1-6 mg | Preferably one of 2 or 2.5 or 3 mg |
| 9 | Methylparaben | 0.1-1.5 mg | Preferably one of 0.7 or 0.9 or 1 mg |

According to a twentieth embodiment of the present disclosure, the multi-dose combination vaccine composition/formulation comprises of:

TABLE 9

| Sr. No. | Formulation Components | Antigen Unit/0.5 ml Dose | Preferred Antigen Unit/0.5 ml Dose (In any of the combination) |
|---|---|---|---|
| 1 | Diphtheria Toxoid (D) | 10-25 Lf | Preferably one of 10 or 20 or 25 Lf |
| 2 | Tetanus toxoid (T) | 02-10 Lf | Preferably one of 2or 4 or 10 Lf |
| 3 | Inactivated *B. pertussis* antigen (wP) | 12-16 IOU | Preferably one of 12 or 14 or 16 IOU |
| 4 | HBs antigen | 7-15 µg | Preferably one of 8 or 10 or 15 µg |
| 5 | Hib PRP-TT conjugate antigen | 7-13 µg of PRP | Preferably one of 8 or 10 or 13 µg of PRP |
| 6 | Inactivated Polio Virus (IPV) Sabin Serotype | | |
|  | Type 1(D antigen units) | 1-50 DU | Preferably one of 5 or 10 or 20 DU |
|  | Type 2 (D antigen units) | 1-50 DU | Preferably one of 8 or 4 or 16 DU |
|  | Type 3(D antigen units) | 1-50 DU | Preferably one of 10 or 16 or 32 DU |
| 7 | Total Aluminium Content ($Al^{3+}$) (as Aluminium Phosphate) | 0.1-0.6 mg | Preferably NMT 0.3 or NMT 0.55 or NMT 0.63 |
| 8 | 2-Phenoxyethanol | 1-6 mg | Preferably one of 2 or 2.5 or 3 mg |
| 9 | Propylparaben | 0.05-0.2 mg | Preferably one of 0.05 or 0.1 or 0.15 mg |

According to a twenty first embodiment of the present disclosure, the multi-dose combination vaccine composition/formulation comprises of:

TABLE 10

| Sr. No. | Formulation Components | Antigen Unit/0.5 ml Dose | Preferred Antigen Unit/0.5 ml Dose (In any of the combination) |
|---|---|---|---|
| 1 | Diphtheria Toxoid (D) | 10-25 Lf | Preferably one of 10 or 20 or 25 Lf |
| 2 | Tetanus toxoid (T) | 02-10 Lf | Preferably one of 2or 4 or 10 Lf |
| 3 | Inactivated *B. pertussis* antigen (wP) | 12-16 IOU | Preferably one of 12 or 14 or 16 IOU |
| 4 | HBs antigen | 7-15 µg | Preferably one of 8 or 10 or 15 µg |
| 5 | Hib PRP-TT conjugate antigen | 7-13 µg of PRP | Preferably one of 8 or 10 or 13 µg of PRP |
| 6 | Inactivated Polio Virus (IPV) Salk Serotype | | |
|  | Mahoney Type 1(D antigen units) | 1-50 DU | Preferably one of 7.5 or 10 or 20 or 40 DU |
|  | MEF-1 Type 2 (D antigen units) | 1-50 DU | Preferably one of 1.5 or 2 or 4 or 8 DU |
|  | Saukett Type 3(D antigen units) | 1-50 DU | Preferably one of 6 or 10 or 16 or 32 DU |
| 7 | Total Aluminium Content ($Al^{3+}$) (as Aluminium Phosphate) | 0.1-0.6 mg | Preferably NMT 0.3 or NMT 0.55 or NMT 0.63 |
| 8 | 2-Phenoxy ethanol | 1-6 mg | Preferably one of 2 or 2.5 or 3 mg |
| 9 | Propylparaben | 0.05-0.2 mg | Preferably one of 0.05 or 0.1 or 0.15 mg |

According to a twenty second embodiment of the present disclosure, the multi-dose combination vaccine composition/formulation comprises of:

TABLE 11

| Sr. No. | Formulation Components | Antigen Unit/0.5 ml Dose | Preferred Antigen Unit/0.5 ml Dose (In any of the combination) |
|---|---|---|---|
| 1 | Diphtheria Toxoid (D) | 10-25 Lf | Preferably one of 10 or 20 or 25 Lf |
| 2 | Tetanus toxoid (T) | 02-10 Lf | Preferably one of 2 or 4 or 10 Lf |
| 3 | Inactivated *B. pertussis* antigen (wP) | 12-16 IOU | Preferably one of 12 or 14 or 16 IOU |
| 4 | HBs antigen | 7-15 µg | Preferably one of 8 or 10 or 15 µg |
| 5 | Hib PRP-TT conjugate antigen | 7-13 µg of PRP | Preferably one of 8 or 10 or 13 µg of PRP |
| 6 | Inactivated Polio Virus (IPV) Sabin Serotype | | |
|   | Type 1(D antigen units) | 1-50 DU | Preferably one of 5 or 10 or 20 DU |
|   | Type 3(D antigen units) | 1-50 DU | Preferably one of 10 or 16 or 32 DU |
| 7 | Total Aluminium Content (Al$^{3+}$) (as Aluminium Phosphate) | 0.1-0.6 mg | Preferably NMT 0.3 or NMT 0.55 or NMT 0.63 |
| 8 | 2-Phenoxyethanol | 1-6 mg | Preferably one of 2 or 2.5 or 3 mg |
| 9 | Propylparaben | 0.05-0.2 mg | Preferably one of 0.05 or 0.1 or 0.15 mg |

According to a twenty third embodiment of the present disclosure, the multi-dose combination vaccine composition/formulation comprises of:

TABLE 12

| Sr. No. | Formulation Components | Antigen Unit/0.5 ml Dose | Preferred Antigen Unit/0.5 ml Dose (In any of the combination) |
|---|---|---|---|
| 1 | Diphtheria Toxoid (D) | 10-25 Lf | Preferably one of 10 or 20 or 25 Lf |
| 2 | Tetanus toxoid (T) | 02-10 Lf | Preferably one of 2 or 4 or 10 Lf |
| 3 | Inactivated *B. pertussis* antigen (wP) | 12-16 IOU | Preferably one of 12 or 14 or 16 IOU |
| 4 | HBs antigen | 7-15 µg | Preferably one of 8 or 10 or 15 µg |
| 5 | Hib PRP-TT conjugate antigen | 7-13 µg of PRP | Preferably one of 8 or 10 or 13 µg of PRP |
| 6 | Inactivated Polio Virus (IPV) Salk Serotype | | |
|   | Mahoney Type 1(D antigen units) | 1-50 DU | Preferably one of 7.5 or 10 or 20 or 40 DU |
|   | Saukett Type 3(D antigen units) | 1-50 DU | Preferably one of 6 or 10 or 16 or 32 DU |
| 7 | Total Aluminium Content (Al$^{3+}$) (as Aluminium Phosphate) | 0.1-0.6 mg | Preferably NMT 0.3 or NMT 0.55 or NMT 0.63 |
| 8 | 2-Phenoxyethanol | 1-6 mg | Preferably one of 2 or 2.5 or 3 mg |
| 9 | Propylparaben | 0.05-0.2 mg | Preferably one of 0.05 or 0.1 or 0.15 mg |

According to a twenty fourth embodiment of the present disclosure, the multi-dose combination vaccine composition/formulation comprises of:

TABLE 13

| Sr. No. | Formulation Components | Antigen Unit/0.5 ml Dose | Preferred Antigen Unit/0.5 ml Dose (In any of the combination) |
|---|---|---|---|
| 1 | Diphtheria Toxoid (D) | 10-25 Lf | Preferably one of 10 or 20 or 25 Lf |
| 2 | Tetanus toxoid (T) | 02-10 Lf | Preferably one of 2 or 4 or 10 Lf |
| 3 | Inactivated *B. pertussis* antigen (wP) | 12-16 IOU | Preferably one of 12 or 14 or 16 IOU |
| 4 | HBs antigen | 7-15 µg | Preferably one of 8 or 10 or 15 µg |
| 5 | Hib PRP-TT conjugate antigen | 7-13 µg of PRP | Preferably one of 8 or 10 or 13 µg of PRP |
| 6 | Inactivated Polio Virus (IPV) Sabin Serotype | | |
|   | Type 1(D antigen units) | 1-50 DU | Preferably one of 5 or 10 or 20 DU |
|   | Type 2 (D antigen units) | 1-50 DU | Preferably one of 8 or 4 or 16 DU |
|   | Type 3(D antigen units) | 1-50 DU | Preferably one of 10 or 16 or 32 DU |
| 7 | Total Aluminium Content (Al$^{3+}$) (as Aluminium Phosphate) | 0.1-0.6 mg | Preferably NMT 0.3 or NMT 0.55 or NMT 0.63 |
| 8 | Methylparaben | 0.1-1.5 mg | Preferably one of 0.7 or 0.9 or 1 mg |
| 9 | Propylparaben | 0.05-0.2 mg | Preferably one of 0.05 or 0.1 or 0.15 mg |

According to a twenty fifth embodiment of the present disclosure, the multi-dose combination vaccine composition/formulation comprises of:

TABLE 14

| Sr. No. | Formulation Components | Antigen Unit/0.5 ml Dose | Preferred Antigen Unit/0.5 ml Dose (In any of the combination) |
|---|---|---|---|
| 1 | Diphtheria Toxoid (D) | 10-25 Lf | Preferably one of 10 or 20 or 25 Lf |
| 2 | Tetanus toxoid (T) | 02-10 Lf | Preferably one of 2 or 4 or 10 Lf |
| 3 | Inactivated *B. pertussis* antigen (wP) | 12-16 IOU | Preferably one of 12 or 14 or 16 IOU |
| 4 | HBs antigen | 7-15 µg | Preferably one of 8 or 10 or 15 µg |
| 5 | Hib PRP-TT conjugate antigen | 7-13 µg of PRP | Preferably one of 8 or 10 or 13 µg of PRP |
| 6 | Inactivated Polio Virus (IPV) Salk Serotype | | |
|  | Mahoney Type 1 (D antigen units) | 1-50 DU | Preferably one of 7.5 or 10 or 20 or 40 DU |
|  | MEF-1 Type 2 (D antigen units) | 1-50 DU | Preferably one of 1.5 or 2 or 4 or 8 DU |
|  | Saukett Type 3 (D antigen units) | 1-50 DU | Preferably one of 6 or 10 or 16 or 32 DU |
| 7 | Total Aluminium Content ($Al^{3+}$) (as Aluminium Phosphate) | 0.1-0.6 mg | Preferably NMT 0.3 or NMT 0.55 or NMT 0.63 |
| 8 | Methylparaben | 0.1-1.5 mg | Preferably one of 0.7 or 0.9 or 1 mg |
| 9 | Propylparaben | 0.05-0.2 mg | Preferably one of 0.05 or 0.1 or 0.15 mg |

According to a twenty sixth embodiment of the present disclosure, the multi-dose combination vaccine composition/formulation comprises of:

TABLE 15

| Sr. No. | Formulation Components | Antigen Unit/0.5 ml Dose | Preferred Antigen Unit/0.5 ml Dose (In any of the combination) |
|---|---|---|---|
| 1 | Diphtheria Toxoid (D) | 10-25 Lf | Preferably one of 10 or 20 or 25 Lf |
| 2 | Tetanus toxoid (T) | 02-10 Lf | Preferably one of 2 or 4 or 10 Lf |
| 3 | Inactivated *B. pertussis* antigen (wP) | 12-16 IOU | Preferably one of 12 or 14 or 16 IOU |
| 4 | HBs antigen | 7-15 µg | Preferably one of 8 or 10 or 15 µg |
| 5 | Hib PRP-TT conjugate antigen | 7-13 µg of PRP | Preferably one of 8 or 10 or 13 µg of PRP |
| 6 | Inactivated Polio Virus (IPV) Sabin Serotype | | |
|  | Type 1 (D antigen units) | 1-50 DU | Preferably one of 5 or 10 or 20 DU |
|  | Type 3 (D antigen units) | 1-50 DU | Preferably one of 10 or 16 or 32 DU |
| 7 | Total Aluminium Content ($Al^{3+}$) (as Aluminium Phosphate) | 0.1-0.6 mg | Preferably NMT 0.3 or NMT 0.55 or NMT 0.63 |
| 8 | Methylparaben | 0.1-1.5 mg | Preferably one of 0.7 or 0.9 or 1 mg |
| 9 | Propylparaben | 0.05-0.2 mg | Preferably one of 0.05 or 0.1 or 0.15 mg |

According to a twenty seventh embodiment of the present disclosure, the multi-dose combination vaccine composition/formulation comprises of:

TABLE 16

| Sr. No. | Formulation Components | Antigen Unit/0.5 ml Dose | Preferred Antigen Unit/0.5 ml Dose (In any of the combination) |
|---|---|---|---|
| 1 | Diphtheria Toxoid (D) | 10-25 Lf | Preferably one of 10 or 20 or 25 Lf |
| 2 | Tetanus toxoid (T) | 02-10 Lf | Preferably one of 2 or 4 or 10 Lf |
| 3 | Inactivated *B. pertussis* antigen (wP) | 12-16 IOU | Preferably one of 12 or 14 or 16 IOU |
| 4 | HBs antigen | 7-15 µg | Preferably one of 8 or 10 or 15 µg |
| 5 | Hib PRP-TT conjugate antigen | 7-13 µg of PRP | Preferably one of 8 or 10 or 13 µg of PRP |

TABLE 16-continued

| Sr. No. | Formulation Components | Antigen Unit/0.5 ml Dose | Preferred Antigen Unit/0.5 ml Dose (In any of the combination) |
|---|---|---|---|
| 6 | Inactivated Polio Virus (IPV) Salk Serotype | | |
| | Mahoney Type 1 (D antigen units) | 1-50 DU | Preferably one of 7.5 or 10 or 20 or 40 DU |
| | Saukett Type 3 (D antigen units) | 1-50 DU | Preferably one of 6 or 10 or 16 or 32 DU |
| 7 | Total Aluminium Content ($Al^{3+}$) (as Aluminium Phosphate) | 0.1-0.6 mg | Preferably NMT 0.3 or NMT 0.55 or NMT 0.63 |
| 8 | Methylparaben | 0.1-1.5 mg | Preferably one of 0.7 or 0.9 or 1 mg |
| 9 | Propylparaben | 0.05-0.2 mg | Preferably one of 0.05 or 0.1 or 0.15 mg |

According to a twenty eight embodiment of the present disclosure, the multi-dose combination vaccine composition/formulation comprises of:

TABLE 17

| Sr. No. | Formulation Components | Antigen Unit/0.5 ml Dose | Preferred Antigen Unit/0.5 ml Dose (In any of the combination) |
|---|---|---|---|
| 1 | Diphtheria Toxoid (D) | 10-25 Lf | Preferably one of 10 or 20 or 25 Lf |
| 2 | Tetanus toxoid (T) | 02-10 Lf | Preferably one of 2 or 4 or 10 Lf |
| 3 | Inactivated B. pertussis antigen (wP) | 12-16 IOU | Preferably one of 12 or 14 or 16 IOU |
| 4 | HBs antigen | 7-15 μg | Preferably one of 8 or 10 or 15 μg |
| 5 | Hib PRP-TT conjugate antigen | 7-13 μg of PRP | Preferably one of 8 or 10 or 13 μg of PRP |
| 6 | Inactivated Polio Virus (IPV) Sabin Serotype | | |
| | Type 1 (D antigen units) | 1-50 DU | Preferably one of 5 or 10 or 20 DU |
| | Type 2 (D antigen units) | 1-50 DU | Preferably one of 8 or 4 or 16 DU |
| | Type 3 (D antigen units) | 1-50 DU | Preferably one of 10 or 16 or 32 DU |
| 7 | Total Aluminium Content ($Al^{3+}$) (as Aluminium Phosphate) | 0.1-0.6 mg | Preferably NMT 0.3 or NMT 0.55 or NMT 0.63 |
| 8 | 2-Phenoxy ethanol | 1-6 mg | Preferably one of 2 or 2.5 or 3 mg |

According to a twenty ninth embodiment of the present disclosure, the multi-dose combination vaccine composition/formulation comprises of:

TABLE 18

| Sr. No. | Formulation Components | Antigen Unit/0.5 ml Dose | Preferred Antigen Unit/0.5 ml Dose (In any of the combination) |
|---|---|---|---|
| 1 | Diphtheria Toxoid (D) | 10-25 Lf | Preferably one of 10 or 20 or 25 Lf |
| 2 | Tetanus toxoid (T) | 02-10 Lf | Preferably one of 2 or 4 or 10 Lf |
| 3 | Inactivated B. pertussis antigen (wP) | 12-16 IOU | Preferably one of 12 or 14 or 16 IOU |
| 4 | HBs antigen | 7-15 μg | Preferably one of 8 or 10 or 15 μg |
| 5 | Hib PRP-TT conjugate antigen | 7-13 μg of PRP | Preferably one of 8 or 10 or 13 μg of PRP |
| 6 | Inactivated Polio Virus (IPV) Salk Serotype | | |
| | Mahoney Type 1 (D antigen units) | 1-50 DU | Preferably one of 7.5 or 10 or 20 or 40 DU |
| | MEF-1 Type 2 (D antigen units) | 1-50 DU | Preferably one of 1.5 or 2 or 4 or 8 DU |
| | Saukett Type 3 (D antigen units) | 1-50 DU | Preferably one of 6 or 10 or 16 or 32 DU |
| 7 | Total Aluminium Content ($Al^{3+}$) (as Aluminium Phosphate) | 0.1-0.6 mg | Preferably NMT 0.3 or NMT 0.55 or NMT 0.63 |
| 8 | 2-Phenoxyethanol | 1-6 mg | Preferably one of 2 or 2.5 or 3 mg |

According to a thirtieth embodiment of the present disclosure, the multi-dose combination vaccine composition/formulation comprises of:

TABLE 19

| Sr. No. | Formulation Components | Antigen Unit/0.5 ml Dose | Preferred Antigen Unit/0.5 ml Dose (In any of the combination) |
|---|---|---|---|
| 1 | Diphtheria Toxoid (D) | 10-25 Lf | Preferably one of 10 or 20 or 25 Lf |
| 2 | Tetanus toxoid (T) | 02-10 Lf | Preferably one of 2 or 4 or 10 Lf |
| 3 | Inactivated *B. pertussis* antigen (wP) | 12-16 IOU | Preferably one of 12 or 14 or 16 IOU |
| 4 | HBs antigen | 7-15 μg | Preferably one of 8 or 10 or 15 μg |
| 5 | Hib PRP-TT conjugate antigen | 7-13 μg of PRP | Preferably one of 8 or 10 or 13 μg of PRP |
| 6 | Inactivated Polio Virus (IPV) Sabin Serotype | | |
|   | Type 1 (D antigen units) | 1-50 DU | Preferably one of 5 or 10 or 20 DU |
|   | Type 3 (D antigen units) | 1-50 DU | Preferably one of 10 or 16 or 32 DU |
| 7 | Total Aluminium Content ($Al^{3+}$) (as Aluminium Phosphate) | 0.1-0.6 mg | Preferably NMT 0.3 or NMT 0.55 or NMT 0.63 |
| 8 | 2-Phenoxyethanol | 1-6 mg | Preferably one of 2 or 2.5 or 3 mg |

According to a thirty first embodiment of the present disclosure, the multi-dose combination vaccine composition/formulation comprises of:

TABLE 20

| Sr. No. | Formulation Components | Antigen Unit/0.5 ml Dose | Preferred Antigen Unit/0.5 ml Dose (In any of the combination) |
|---|---|---|---|
| 1 | Diphtheria Toxoid (D) | 10-25 Lf | Preferably one of 10 or 20 or 25 Lf |
| 2 | Tetanus toxoid (T) | 02-10 Lf | Preferably one of 2 or 4 or 10 Lf |
| 3 | Inactivated *B. pertussis* antigen (wP) | 12-16 IOU | Preferably one of 12 or 14 or 16 IOU |
| 4 | HBs antigen | 7-15 μg | Preferably one of 8 or 10 or 15 μg |
| 5 | Hib PRP-TT conjugate antigen | 7-13 μg of PRP | Preferably one of 8 or 10 or 13 μg of PRP |
| 6 | Inactivated Polio Virus (IPV) Salk Serotype | | |
|   | Mahoney Type 1 (D antigen units) | 1-50 DU | Preferably one of 7.5 or 10 or 20 or 40 DU |
|   | Saukett Type 3 (D antigen units) | 1-50 DU | Preferably one of 6 or 10 or 16 or 32 DU |
| 7 | Total Aluminium Content ($Al^{3+}$) (as Aluminium Phosphate) | 0.1-0.6 mg | Preferably NMT 0.3 or NMT 0.55 or NMT 0.63 |
| 8 | 2-Phenoxy ethanol | 1-6 mg | Preferably one of 2 or 2.5 or 3 mg |

According to a thirty second embodiment of the present disclosure, the final single-dose combination vaccine composition/formulation comprises of:

TABLE 21

| Sr. No. | Formulation Components | Antigen Unit/0.5 ml Dose | Preferred Antigen Unit/0.5 ml Dose (In any of the combination) |
|---|---|---|---|
| 1 | Diphtheria Toxoid (D) | 10-25 Lf | Preferably one of 10 or 20 or 25 Lf |
| 2 | Tetanus toxoid (T) | 02-10 Lf | Preferably one of 2 or 4 or 10 Lf |
| 3 | Inactivated *B. pertussis* antigen (wP) | 12-16 IOU | Preferably one of 12 or 14 or 16 IOU |
| 4 | HBs antigen | 7-15 μg | Preferably one of 8 or 10 or 15 μg |
| 5 | Hib PRP-TT conjugate antigen | 7-13 μg of PRP | Preferably one of 8 or 10 or 13 μg of PRP |
| 6 | Inactivated Polio Virus (IPV) Sabin Serotype | | |
|   | Type 1 (D antigen units) | 1-50 DU | Preferably one of 5 or 10 or 20 DU |
|   | Type 2 (D antigen units) | 1-50 DU | Preferably one of 8 or 4 or 16 DU |
|   | Type 3 (D antigen units) | 1-50 DU | Preferably one of 10 or 16 or 32 DU |
| 7 | Total Aluminium Content ($Al^{3+}$) (as Aluminium Phosphate) | 0.1-0.6 mg | Preferably NMT 0.3 or NMT 0.55 or NMT 0.63 |

According to a thirty third embodiment of the present disclosure, the final single-dose combination vaccine composition/formulation comprises of:

TABLE 22

| Sr. No. | Formulation Components | Antigen Unit/0.5 ml Dose | Preferred Antigen Unit/0.5 ml Dose (In any of the combination) |
|---|---|---|---|
| 1 | Diphtheria Toxoid (D) | 10-25 Lf | Preferably one of 10 or 20 or 25 Lf |
| 2 | Tetanus toxoid (T) | 02-10 Lf | Preferably one of 2 or 4 or 10 Lf |
| 3 | Inactivated B. pertussis antigen (wP) | 12-16 IOU | Preferably one of 12 or 14 or 16 IOU |
| 4 | HBs antigen | 7-15 μg | Preferably one of 8 or 10 or 15 μg |
| 5 | Hib PRP-TT conjugate antigen | 7-13 μg of PRP | Preferably one of 8 or 10 or 13 μg of PRP |
| 6 | Inactivated Polio Virus (IPV) Salk Serotype | | |
|  | Mahoney Type 1 (D antigen units) | 1-50 DU | Preferably one of 7.5 or 10 or 20 or 40 DU |
|  | MEF-1 Type 2 (D antigen units) | 1-50 DU | Preferably one of 1.5 or 2 or 4 or 8 DU |
|  | Saukett Type 3 (D antigen units) | 1-50 DU | Preferably one of 6 or 10 or 16 or 32 DU |
| 7 | Total Aluminium Content ($Al^{3+}$) (as Aluminium Phosphate) | 0.1-0.6 mg | Preferably NMT 0.3 or NMT 0.55 or NMT 0.63 |

According to a thirty forth embodiment of the present disclosure, the final single-dose combination vaccine composition/formulation comprises of:

TABLE 23

| Sr. No. | Formulation Components | Antigen Unit/0.5 ml Dose | Preferred Antigen Unit/0.5 ml Dose (In any of the combination) |
|---|---|---|---|
| 1 | Diphtheria Toxoid (D) | 10-25 Lf | Preferably one of 10 or 20 or 25 Lf |
| 2 | Tetanus toxoid (T) | 02-10 Lf | Preferably one of 2 or 4 or 10 Lf |
| 3 | Inactivated B. pertussis antigen (wP) | 12-16 IOU | Preferably one of 12 or 14 or 16 IOU |
| 4 | HBs antigen | 7-15 μg | Preferably one of 8 or 10 or 15 μg |
| 5 | Hib PRP-TT conjugate antigen | 7-13 μg of PRP | Preferably one of 8 or 10 or 13 μg of PRP |
| 6 | Inactivated Polio Virus (IPV) Sabin Serotype | | |
|  | Type 1 (D antigen units) | 1-50 DU | Preferably one of 5 or 10 or 20 DU |
|  | Type 3 (D antigen units) | 1-50 DU | Preferably one of 10 or 16 or 32 DU |
| 7 | Total Aluminium Content ($Al^{3+}$) (as Aluminium Phosphate) | 0.1-0.6 mg | Preferably NMT 0.3 or NMT 0.55 or NMT 0.63 |

According to a thirty fifth embodiment of the present disclosure, the final single-dose combination vaccine composition/formulation comprises of:

TABLE 24

| Sr. No. | Formulation Components | Antigen Unit/0.5 ml Dose | Preferred Antigen Unit/0.5 ml Dose (In any of the combination) |
|---|---|---|---|
| 1 | Diphtheria Toxoid (D) | 10-25 Lf | Preferably one of 10 or 20 or 25 Lf |
| 2 | Tetanus toxoid (T) | 02-10 Lf | Preferably one of 2 or 4 or 10 Lf |
| 3 | Inactivated B. pertussis antigen (wP) | 12-16 IOU | Preferably one of 12 or 14 or 16 IOU |
| 4 | HBs antigen | 7-15 μg | Preferably one of 8 or 10 or 15 μg |
| 5 | Hib PRP-TT conjugate antigen | 7-13 μg of PRP | Preferably one of 8 or 10 or 13 μg of PRP |
| 6 | Inactivated Polio Virus (IPV) Salk Serotype | | |
|  | Mahoney Type 1 (D antigen units) | 1-50 DU | Preferably one of 7.5 or 10 or 20 or 40 DU |
|  | Saukett Type 3 (D antigen units) | 1-50 DU | Preferably one of 6 or 10 or 16 or 32 DU |
| 7 | Total Aluminium Content ($Al^{3+}$) (as Aluminium Phosphate) | 0.1-0.6 mg | Preferably NMT 0.3 or NMT 0.55 or NMT 0.63 |

NMT—Not More Than

According to a thirty sixth embodiment of the present disclosure, one or more antigens of the final combination vaccine composition may not be substantially adsorbed on to any adjuvant.

According to a thirty seventh embodiment of the present disclosure, the pH of the immunogenic composition may be in the range of pH 6.0 to pH 8.0; more preferably in the range of pH 6.0 to pH 7.5; still more preferably in the range of pH 6.2 to pH 7.2; and most preferably in the range of pH 6.3 to pH 6.8.

According to thirty eighth embodiment of the present disclosure, the immunogenic composition may additionally comprise of a buffering agent selected from the group consisting of carbonate, phosphate, acetate, succinate, borate, citrate, lactate, gluconate and tartrate, as well as more complex organic buffering agents including a phosphate buffering agent that contains sodium phosphate and/or potassium phosphate in a ratio selected to achieve the desired pH. In another example, the buffering agent contains Tris (hydroxymethyl) aminomethane, or "Tris", formulated to achieve the desired pH. Yet in another example, the buffering agent could be the minimum essential medium with Hanks salts. Other buffers, such as HEPES, piperazine-N, N'-bis (PIPES), and 2-ethanesulfonic acid (MES) are also envisaged by the present disclosure. The buffer aids in stabilizing the immunogenic composition of the present disclosure. The amount of the buffer may be in the range of 0.1 mM to 100 mM, preferably selected from 5 mM, 6 mM, 7 mM, 22 mM, 23 mM, 24 mM, 25 mM, 26 mM, 27 mM, 28 mM, 29 mM and 30 mM.

Yet another aspect of the embodiment, the immunogenic composition may additionally comprise of pharmaceutically acceptable excipients selected from the group consisting of surfactants, polymers and salts. Examples of Surfactants may include non-ionic surfactants such as polysorbate 20, polysorbate 80, etc. Examples of the polymers may include dextran, carboxymethyl cellulose, hyaluronic acid, cyclodextrin, etc. Examples of the salts may include NaCl, KCl, $KH_2PO_4$, $Na_2HPO_4.2H_2O$, $CaCl_2$, $MgCl_2$, etc. Preferably, the salt may be NaCl. Typically the amount of the salt may be in the range of 100 mM to 200 mM.

Amino acids, such as Histidine, glycine, arginine and lysine may be added to stabilize the immunogenic composition.

According to a thirty ninth embodiment of the present disclosure, the immunogenic composition may additionally comprise of one or more adjuvant selected from the group of aluminium salt (Al3+) such as aluminium hydroxide (Al(OH)$_3$) or aluminium phosphate (AlPO$_4$), alum, calcium phosphate, MPLA, 3D-MPL, QS21, a CpG-containing oligodeoxynucleotide adjuvant, liposome, or oil-in-water emulsion.

Yet preferably the composition comprises aluminium phosphate (AlPO$_4$) as adjuvant.

Yet preferably the composition comprises aluminium hydroxide (AlOH3) as adjuvant.

In one of the aspect of the thirty ninth embodiment, antigens of the final formulation may be adsorbed on to insitu aluminium phosphate gel or readymade Aluminium phosphate gel or a combination thereof.

In one of the preferred aspect of the thirty ninth embodiment, the composition of the present disclosure may contain the adjuvant in an amount of 2.5 mg/0.5 ml or less, and specifically, in an amount of 1.5 mg/0.5 ml to 0.1 mg/0.5 ml.

According to a fortieth embodiment of the present disclosure, the immunogenic composition may additionally comprise of an immunostimulatory component selected from the group consisting of an oil and water emulsion, MF-59, a liposome, a lipopolysaccharide, a saponin, lipid A, lipid A derivatives, Monophosphoryl lipid A, 3-deacylated monophosphoryl lipid A, AS01, AS03, an oligonucleotide, an oligonucleotide comprising at least one unmethylated CpG and/or a liposome, Freund's adjuvant, Freund's complete adjuvant, Freund's incomplete adjuvant, polymers, co-polymers such as polyoxyethylene-polyoxypropylene copolymers, including block co-polymers, polymer p 1005, CRL-8300 adjuvant, muramyl dipeptide, TLR-4 agonists, flagellin, flagellins derived from gram negative bacteria, TLR-5 agonists, fragments of flagellins capable of binding to TLR-5 receptors, Alpha-C-galactosylceramide, Chitosan, Interleukin-2, QS-21, ISCOMS, squalene mixtures (SAF-1), Quil A, cholera toxin B subunit, polyphosphazene and derivatives, mycobacterium cell wall preparations, mycolic acid derivatives, non-ionic block copolymer surfactants, OMV, fHbp, saponin combination with sterols and lipids.

According to a forty first embodiment of the present disclosure, the immunogenic composition may additionally comprise of preservative selected from the group consisting of Benzethonium chloride (Phemerol), Phenol, m-cresol, Thiomersal, Formaldehyde, benzalkonium chloride, benzyl alcohol, chlorobutanol, p-chlor-m-cresol, or benzyl alcohol or a combination thereof. A vaccine composition may include preservative for a single immunization, or may include preservative for multiple immunizations (i.e. a 'multidose' kit). The inclusion of a preservative is preferred in multidose arrangements. As an alternative (or in addition) to including a preservative in multidose compositions, the compositions may be contained in a container having an aseptic adaptor for removal of material. Typically the amount of the preservative may be in the range of 0.1 mg to 50 mg.

According to a forty second embodiment of the present disclosure, the immunogenic composition may additionally comprise of auxiliary substances such as wetting or emulsifying agents, pH buffering agents, gelling or viscosity enhancing additives, flavoring agents, colors, and the like, depending upon the route of administration and the preparation desired.

According to a forty third embodiment of the present disclosure, the immunogenic composition may be fully liquid but is not limited thereto. Suitable forms of liquid preparation may include solutions, suspensions, emulsions, syrups, isotonic aqueous solutions, viscous compositions and elixirs that are buffered to a desired pH.

The immunogenic composition of the present disclosure may be in the form of transdermal preparations including lotions, gels, sprays, ointments or other suitable techniques. If nasal or respiratory (mucosal) administration is desired (e.g., aerosol inhalation or insufflation), compositions can be in a form and dispensed by a squeeze spray dispenser, pump dispenser or aerosol dispenser. Aerosols are usually under pressure by means of a hydrocarbon. Pump dispensers can preferably dispense a metered dose or a dose having a particular particle size. When in the form of solutions, suspensions and gels, in some embodiments, the immunogenic compositions contain a major amount of water (preferably purified water) in addition to the active ingredient(s).

According to a forty forth embodiment of the present disclosure, the said combination vaccine may be stable at 2-8 deg C. for 12 to 36 months; at 25 deg C. for 2 to 6 months; at 37 deg C. for 1 week to 4 weeks.

According to a forty fifth embodiment of the present disclosure, the immunogenic composition may be formulated for use in a method for reducing the onset of or preventing a health condition comprising diphtheria, tetanus, pertussis, hepatitis B virus, *Haemophilus influenzae* type b, polio virus infection involving administration of an immunologically effective amount of the immunogenic composition to a human subject via parenteral or subcutaneous or intradermal, intramuscular or intraperitoneal or intravenous administration or injectable administration or sustained release from implants or administration by eye drops or nasal or rectal or buccal or vaginal, peroral or intragastric or mucosal or perlinqual, alveolar or gingival or olfactory or respiratory mucosa administration or any other routes of immunization.

According to forty sixth embodiment of the present disclosure, the immunogenic composition could be formulated as single dose vials or multidose vials (2 Dose or 5 Dose or 10 Dosevials) or multidose kit or as pre-filled syringes wherein the said immunogenic composition may be given in a single dose schedule, or preferably a multiple dose schedule in which a primary course of vaccination is followed by 1-3 separate doses given at subsequent time intervals after 1-3 years if needed. The dosage regimen will also, at least in part, be determined on the need of a booster dose required to confer protective immunity.

Yet preferably the immunogenic composition may be formulated for administration to a human subject or children 2 years of age or below according to a two dose regimens consisting of a first dose, and second dose at subsequent time intervals after 1-3 years.

Yet preferably the immunogenic composition may be administered concomitantly with other drugs or any other vaccine.

According to a forty seventh embodiment of the present disclosure, applicant has found that a multi-dose fully liquid combination vaccine with improved immunogenicity and reduced reactogenicity can be obtained when vaccine is manufactured by process disclosed below taking into consideration i) process of making individual antigens ii)sequence of addition of the antigens iii) the use of the specific adjuvants in a specific quantity for certain antigens, iv) individual adsorption or combined adsorption of antigens onto adjuvants v) Degree of adsorption of antigen onto adjuvants vi) using minimum Alum concentration vii) using optimal concentration and type of preservative and viii) use of various parameters including agitation, temperature and pH.

Biological Source of Strains used in SIIPL Combination Vaccine:

Diphtheria Toxoid:

The strain *Corynebacterium diphtheriae* PW8 CN2000 was obtained from the Wellcome Research Laboratory, London, United Kingdom by the National Control Authority Central Research Institute (C.R.I.) Kasauli, Himachal Pradesh, India in lyophilized form in the year 1973.The strain was revived and further lyophilized under Master Seed Lot-*C. diphtheriae* CN2000 A1 at C.R.I. Kasauli.

Tetanus Toxoid:

The strain *Clostridium tetani* Harvard Strain No.49205 was obtained from The Rijks Institute Voor de Volksgezondheid (Netherlands) by the National Control Authority C.R.I. Kasauli, in Lyophilized form.

Pertussis:

Manufacturing of Pertussis vaccine bulk at SIIPL involves usage of four strains of Bordetella pertussis viz. Strains 134, 509, 6229 and 25525.The Master Seed of Strains 134 and 509 are originally from Rijks Institute, The Netherlands, obtained through National Control Authority, Central Research Institute, Kasauli, Himachal Pradesh, India. The Master Seed of Strains 6229 and 25525 are originally from Lister Institute, England.

Hepatitis B:

Rhein Biotech (Germany) constructed the recombinant Hansenulapolymorpha strain containing the HBsAg surface antigen gene. Rhein Biotech also made the Master Cell Bank (MCB Hansenulapolymorpha K3/8-1 strain ADW, 12/94) and performed all the characterization tests on this bank.

*Haemophilus influenzae* Type b:

The source organism for generation of cell substrate is *Haemophilus influenzae* type b, strain 760705. The strain was originally isolated from a 2 year and 2 months old baby boy (born on 14 Aug. 74) in November 1976.Three passages of the strain took place before storage at −70° C. at the Academic Medical Centre (AMC), University of Amsterdam. This strain was transferred to SIIPL as a part of collaboration between SIIPL and Netherlands Vaccines Institute (NVI, The Netherlands).

IPV:

The strain and source of Salk poliovirus is given below.

Poliovirus type 1:
Strain: Mahoney
Source: Bilthoven Biologicals, Netherlands

Poliovirus type 2:
Strain: MEF1
Source: Bilthoven Biologicals, Netherlands

Poliovirus type 3:
Strain: Saukett
Source: Bilthoven Biologicals, Netherlands

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The use of the expression "at least" or "at least one" suggests the use of one or more elements or ingredients or quantities, as the use may be in the embodiment of the invention to achieve one or more of the desired objects or results. While certain embodiments of the inventions have been described, these embodiments have been presented by way of example only, and are not intended to limit the scope of the inventions. Variations or modifications to the formulation of this invention, within the scope of the invention, may occur to those skilled in the art upon reviewing the disclosure herein. Such variations or modifications are well within the spirit of this invention.

The numerical values given for various physical parameters, dimensions and quantities are only approximate values and it is envisaged that the values higher than the numerical value assigned to the physical parameters, dimensions and quantities fall within the scope of the invention unless there is a statement in the specification to the contrary.

While considerable emphasis has been placed herein on the specific features of the preferred embodiment, it will be appreciated that many additional features can be added and that many changes can be made in the preferred embodiment without departing from the principles of the disclosure. These and other changes in the preferred embodiment of the disclosure will be apparent to those skilled in the art from the disclosure herein, whereby it is to be distinctly understood that the foregoing descriptive matter is to be interpreted merely as illustrative of the disclosure and not as a limitation.

Advantages

The present disclosure described herein above has several technical advances and advantages including, but not limited to, the realization of a combination vaccine composition comprising D, T, wP, HBsAg, Hib PRP-TT conjugate and IPV and the method of manufacturing the same. When compared to other combination vaccine composition, the present disclosure provides the following advantages:
1. Fully liquid combination vaccine
2. Reduced dose of IPV antigen as compared to standard dose showing comparable efficacy as compared to standard dose (40-8-32 DU)
3. Improved immunogenicity of D, T, wP, HepB, Hib, IPV antigen
4. Improved stability at 2-8° C. and room temperature tested over a period of 12 months
5. A highly purified Diphtheria toxoids (D) & tetanus toxoids (T) produced using semi synthetic medium free of Transmissible Spongiform Encephalopathy (TSE) or Bovine Spongiform Encephalopathy (BSE).
6. Whole-cell *B. pertussis* (wP) antigen comprises *Bordetella pertussis* strains 134, 509, 25525 and 6229 in a ratio of 1:1:0.25:0.25 thereby improving potency and immunogenicity against *B. pertussis*.
7. Improved method of inactivation of whole-cell *B. pertussis* (wP) component using combination of heat and formaldehyde inactivation. The process is devoid of thiomersal and inactivated whole cell pertussis antigen remains non-clumpy and homogeneous thereby leading to reduced reactogenicity and giving better potency for a longer duration.
8. Low Free PRP (less than 7%) in the Total *Haemophilus influenzae* Type b PRP-TT conjugate bulk
9. The percentage of adsorption of Hib antigen on to any adjuvant is less than 20%.
10. Improved adsorption profile of Diphtheria toxoid antigen (D), tetanus toxoid (T) antigen and Hepatitis B (HepB) surface antigen adsorbed individually onto aluminium phosphate adjuvant thereby improving potency and immunogenicity.
11. Minimum total alum content ($Al^{3+}$) thereby ensuring reduced reactogenicity.
12. Optimized concentration of 2-phenoxyethanol (2-PE) and at least one paraben ester (methylparaben or propylparaben) as preservative therefore maintaining the antimicrobial ability of a multiple-dose fully liquid combination vaccine effectively.

EXAMPLES

The following examples are included to demonstrate preferred embodiments of the invention. It should be appreciated by those of skill in the art that the compositions and techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1: Various Combinations of Vaccine Compositions in Accordance with the Present Disclosure

TABLE 25

| Combination Vaccine comprising IPV (Salk Strain type 1(Mahoney) or type 2(MEF) or type 3(Saukett)) | | | | | | | | | | | | |
|---|---|---|---|---|---|---|---|---|---|---|---|---|
| S. Formulation | Combination composition in accordance with the present disclosure [per 0.5 ml Dose] | | | | | | | | | | | |
| No. Components | 1 | 2 | 3 | 4 | 5 | 6 | 7 | 8 | 9 | 10 | 11 | 12 |
| 1 Diphtheria Toxoid (D) | 10 Lf | 10 Lf | 10 Lf | 10 Lf | 10 Lf | 10 Lf | 10 Lf | 10 Lf | 20 Lf | 20 Lf | 20 Lf | 20 Lf |
| 2 Tetanus toxoid (T) | 02 Lf | 02 Lf | 02 Lf | 02 Lf | 02 Lf | 02 Lf | 02 Lf | 02 Lf | 4 Lf | 4 Lf | 4 Lf | 4 Lf |
| 3 Inactivated B. pertussis antigen (wP) | 12 IOU | 12 IOU | 12 IOU | 12 IOU | 12 IOU | 12 IOU | 12 IOU | 12 IOU | 14 IOU | 14 IOU | 14 IOU | 14 IOU |
| 4 HBs antigen | 8 µg | 8 µg | 8 µg | 8 µg | 8 µg | 8 µg | 8 µg | 8 µg | 15 µg | 15 µg | 15 µg | 15 µg |
| 5 Hib PRP-TT conjugate antigen | 8 µg of PRP | 8 µg of PRP | 8 µg of PRP | 8 µg of PRP | 8 µg of PRP | 8 µg of PRP | 8 µg of PRP | 8 µg of PRP | 10 µg of PRP | 10 µg of PRP | 10 µg of PRP | 10 µg of PRP |
| 6 Inactivated Polio Virus (IPV) Type 1 (D antigen units) | 7.5 or 10 or 20 or 40 | 7.5 or 10 or 20 or 40 | 7.5 or 10 or 20 or 40 | 7.5 or 10 or 20 or 40 | 7.5 or 10 or 20 or 40 | 7.5 or 10 or 20 or 40 | 7.5 or 10 or 20 or 40 | 7.5 or 10 or 20 or 40 | 7.5 or 10 or 20 or 40 | 7.5 or 10 or 20 or 40 | 7.5 or 10 or 20 or 40 | 7.5 or 10 or 20 or 40 |
| Type 2 (D antigen units) | 1.5 or 2 or 4 or 8 | — | 1.5 or 2 or 4 or 8 | — | 1.5 or 2 or 4 or 8 | — | 1.5 or 2 or 4 or 8 | — | 1.5 or 2 or 4 or 8 | — | 1.5 or 2 or 4 or 8 | — |
| Type 3 (D antigen units) | 6 or 10 or 16 or 32 | 6 or 10 or 16 or 32 | 6 or 10 or 16 or 32 | 6 or 10 or 16 or 32 | 6 or 10 or 16 or 32 | 6 or 10 or 16 or 32 | 6 or 10 or 16 or 32 | 6 or 10 or 16 or 32 | 6 or 10 or 16 or 32 | 6 or 10 or 16 or 32 | 6 or 10 or 16 or 32 | 6 or 10 or 16 or 32 |

TABLE 25-continued

Combination Vaccine comprising IPV (Salk Strain type 1(Mahoney) or type 2(MEF) or type 3(Saukett))

| 7 | Total Aluminium Content (Al³⁺) (as Aluminium Phosphate) | Not more than 0.55 mg | Not more than 0.55 mg | Not more than 0.55 mg | Not more than 0.55 mg | Not more than 0.55 mg | Not more than 0.55 mg | Not more than 0.55 mg | Not more than 0.55 mg | Not more than 0.55 mg | Not more than 0.55 mg | Not more than 0.55 mg | Not more than 0.55 mg |
| 8 | 2-Phenoxyethanol | 2.5 mg | 2.5 mg | 2.5 mg | 2.5 mg | 2.5 mg | 2.5 mg | 2.5 mg | 2.5 mg | 2.5 mg | 2.5 mg | 2.5 mg | 2.5 mg |
| 9 | Methylparaben | 0.9 mg | 0.9 mg | 0.9 mg | 0.9 mg | — | — | — | — | 0.9 mg | 0.9 mg | 0.9 mg | 0.9 mg |
| 10 | Propylparaben | 0.1 mg | 0.1 mg | — | — | 0.1 mg | 0.1 mg | — | — | 0.1 mg | 0.1 mg | — | — |

| S. No. | Formulation Components | Combination composition in accordance with the present disclosure [per 0.5 ml Dose] | | | | | | | | | | | |
|---|---|---|---|---|---|---|---|---|---|---|---|---|
| | | 13 | 14 | 15 | 16 | 17 | 18 | 19 | 20 | 21 | 22 | 23 | 24 |
| 1 | Diphtheria Toxoid (D) | 20 Lf | 20 Lf | 20 Lf | 20 Lf | 25 Lf | 25 Lf | 25 Lf | 25 Lf | 25 Lf | 25 Lf | 25 Lf | 25 Lf |
| 2 | Tetanus toxoid (T) | 4 Lf | 4 Lf | 4 Lf | 4 Lf | 10 Lf | 10 Lf | 10 Lf | 10 Lf | 10 Lf | 10 Lf | 10 Lf | 10 Lf |
| 3 | Inactivated B. pertussis antigen (wP) | 14 IOU | 14 IOU | 14 IOU | 14 IOU | 16 IOU | 16 IOU | 16 IOU | 16 IOU | 16 IOU | 16 IOU | 16 IOU | 16 IOU |
| 4 | HBs antigen | 15 µg | 15 µg | 15 µg | 15 µg | 15 µg | 15 µg | 15 µg | 15 µg | 15 µg | 15 µg | 15 µg | 15 µg |
| 5 | Hib PRP-TT conjugate antigen | 10 µg of PRP | 10 µg of PRP | 10 µg of PRP | 10 µg of PRP | 13 µg of PRP | 13 µg of PRP | 13 µg of PRP | 13 µg of PRP | 13 µg of PRP | 13 µg of PRP | 13 µg of PRP | 13 µg of PRP |
| 6 | Inactivated Polio Virus (IPV) | | | | | | | | | | | | |
| | Type 1 (D antigen units) | 7.5 or 10 or 20 or 40 | 7.5 or 10 or 20 or 40 | 7.5 or 10 or 20 or 40 | 7.5 or 10 or 20 or 40 | 7.5 or 10 or 20 or 40 | 7.5 or 10 or 20 or 40 | 7.5 or 10 or 20 or 40 | 7.5 or 10 or 20 or 40 | 7.5 or 10 or 20 or 40 | 7.5 or 10 or 20 or 40 | 7.5 or 10 or 20 or 40 | 7.5 or 10 or 20 or 40 |
| | Type 2 (D antigen units) | 1.5 or 2 or 4 or 8 | — | 1.5 or 2 or 4 or 8 | — | 1.5 or 2 or 4 or 8 | — | 1.5 or 2 or 4 or 8 | — | 1.5 or 2 or 4 or 8 | — | 1.5 or 2 or 4 or 8 | — |
| | Type 3 (D antigen units) | 6 or 10 or 16 or 32 | 6 or 10 or 16 or 32 | 6 or 10 or 16 or 32 | 6 or 10 or 16 or 32 | 6 or 10 or 16 or 32 | 6 or 10 or 16 or 32 | 6 or 10 or 16 or 32 | 6 or 10 or 16 or 32 | 6 or 10 or 16 or 32 | 6 or 10 or 16 or 32 | 6 or 10 or 16 or 32 | 6 or 10 or 16 or 32 |
| 7 | Total Aluminium Content (Al³⁺) (as Aluminium Phosphate) | Not more than 0.55 mg | Not more than 0.55 mg | Not more than 0.55 mg | Not more than 0.55 mg | Not more than 0.55 mg | Not more than 0.55 mg | Not more than 0.55 mg | Not more than 0.55 mg | Not more than 0.55 mg | Not more than 0.55 mg | Not more than 0.55 mg | Not more than 0.55 mg |
| 8 | 2-Phenoxyethanol | 2.5 mg | 2.5 mg | 2.5 mg | 2.5 mg | 2.5 mg | 2.5 mg | 2.5 mg | 2.5 mg | 2.5 mg | 2.5 mg | 2.5 mg | 2.5 mg |
| 9 | Methylparaben | — | — | — | — | 0.9 mg | 0.9 mg | 0.9 mg | 0.9 mg | — | — | — | — |
| 10 | Propylparaben | 0.1 mg | 0.1 mg | — | — | 0.1 mg | 0.1 mg | — | — | 0.1 mg | 0.1 mg | — | — |

Additionally adjusting the pH of the composition as disclosed above to about 6.0 to 7.0 with Sodium Hydroxide/Sodium Carbonate and make up the volume by adding normal saline (0.9%). The vaccine may contain traces of glutaraldehyde, formaldehyde, neomycin, streptomycin and polymixin B which are used during the manufacturing process.

TABLE 26

Combination Vaccine comprising IPV (Sabin Strain: Type 1, Type 2 & Type 3)

| S. No. | Formulation Components | Combination composition in accordance with the present disclosure [per 0.5 ml Dose] | | | | | | | | | | | |
|---|---|---|---|---|---|---|---|---|---|---|---|---|
| | | 1 | 2 | 3 | 4 | 5 | 6 | 7 | 8 | 9 | 10 | 11 | 12 |
| 1 | Diphtheria Toxoid (D) | 10 Lf | 10 Lf | 10 Lf | 10 Lf | 10 Lf | 10 Lf | 10 Lf | 10 Lf | 20 Lf | 20 Lf | 20 Lf | 20 Lf |
| 2 | Tetanus toxoid (T) | 02 Lf | 02 Lf | 02 Lf | 02 Lf | 02 Lf | 02 Lf | 02 Lf | 02 Lf | 4 Lf | 4 Lf | 4 Lf | 4 Lf |
| 3 | Inactivated B. pertussis antigen (wP) | 12 IOU | 12 IOU | 12 IOU | 12 IOU | 12 IOU | 12 IOU | 12 IOU | 12 IOU | 14 IOU | 14 IOU | 14 IOU | 14 IOU |
| 4 | HBs antigen | 8 μg | 8 μg | 8 μg | 8 μg | 8 μg | 8 μg | 8 μg | 8 μg | 15 μg | 15 μg | 15 μg | 15 μg |
| 5 | Hib PRP-TT conjugate antigen | 8 μg of PRP | 8 μg of PRP | 8 μg of PRP | 8 μg of PRP | 8 μg of PRP | 8 μg of PRP | 8 μg of PRP | 8 μg of PRP | 10 μg of PRP | 10 μg of PRP | 10 μg of PRP | 10 μg of PRP |
| 6 | Inactivated Polio Virus (IPV) Type 1 (D antigen units) | 5 or 10 or 20 | 5 or 10 or 20 | 5 or 10 or 20 | 5 or 10 or 20 | 5 or 10 or 20 | 5 or 10 or 20 | 5 or 10 or 20 | 5 or 10 or 20 | 5 or 10 or 20 | 5 or 10 or 20 | 5 or 10 or 20 | 5 or 10 or 20 |
| | Type 2 (D antigen units) | 4 or 8 or 16 | — | 4 or 8 or 16 | — | 4 or 8 or 16 | — | 4 or 8 or 16 | — | 4 or 8 or 16 | — | 4 or 8 or 16 | — |
| | Type 3 (D antigen units) | 10 or 16 or 32 | 10 or 16 or 32 | 10 or 16 or 32 | 10 or 16 or 32 | 10 or 16 or 32 | 10 or 16 or 32 | 10 or 16 or 32 | 10 or 16 or 32 | 10 or 16 or 32 | 10 or 16 or 32 | 10 or 16 or 32 | 10 or 16 or 32 |
| 7 | Total Aluminium Content ($Al^{3+}$) (as Aluminium Phosphate) | Not more than 0.55 mg | Not more than 0.55 mg | Not more than 0.55 mg | Not more than 0.55 mg | Not more than 0.55 mg | Not more than 0.55 mg | Not more than 0.55 mg | Not more than 0.55 mg | Not more than 0.55 mg | Not more than 0.55 mg | Not more than 0.55 mg | Not more than 0.55 mg |
| 8 | 2-Phenoxyethanol | 2.5 mg | 2.5 mg | 2.5 mg | 2.5 mg | 2.5 mg | 2.5 mg | 2.5 mg | 2.5 mg | 2.5 mg | 2.5 mg | 2.5 mg | 2.5 mg |
| 9 | Methylparaben | 0.9 mg | 0.9 mg | 0.9 mg | 0.9 mg | — | — | — | — | 0.9 mg | 0.9 mg | 0.9 mg | 0.9 mg |
| 10 | Propylparaben | 0.1 mg | 0.1 mg | — | — | 0.1 mg | 0.1 mg | — | — | 0.1 mg | 0.1 mg | — | — |

| S. No. | Formulation Components | Combination composition in accordance with the present disclosure [per 0.5 ml Dose] | | | | | | | | | | | |
|---|---|---|---|---|---|---|---|---|---|---|---|---|
| | | 13 | 14 | 15 | 16 | 17 | 18 | 19 | 20 | 21 | 22 | 23 | 24 |
| 1 | Diphtheria Toxoid (D) | 20 Lf | 20 Lf | 20 Lf | 20 Lf | 25 Lf | 25 Lf | 25 Lf | 25 Lf | 25 Lf | 25 Lf | 25 Lf | 25 Lf |
| 2 | Tetanus toxoid (T) | 4 Lf | 4 Lf | 4 Lf | 4 Lf | 10 Lf | 10 Lf | 10 Lf | 10 Lf | 10 Lf | 10 Lf | 10 Lf | 10 Lf |
| 3 | Inactivated B. pertussis antigen (wP) | 14 IOU | 14 IOU | 14 IOU | 14 IOU | 16 IOU | 16 IOU | 16 IOU | 16 IOU | 16 IOU | 16 IOU | 16 IOU | 16 IOU |
| 4 | HBs antigen | 15 μg | 15 μg | 15 μg | 15 μg | 15 μg | 15 μg | 15 μg | 15 μg | 15 μg | 15 μg | 15 μg | 15 μg |
| 5 | Hib PRP-TT conjugate antigen | 10 μg of PRP | 10 μg of PRP | 10 μg of PRP | 10 μg of PRP | 13 μg of PRP | 13 μg of PRP | 13 μg of PRP | 13 μg of PRP | 13 μg of PRP | 13 μg of PRP | 13 μg of PRP | 13 μg of PRP |
| 6 | Inactivated Polio Virus (IPV) Type 1 (D antigen units) | 5 or 10 or 20 | 5 or 10 or 20 | 5 or 10 or 20 | 5 or 10 or 20 | 5 or 10 or 20 | 5 or 10 or 20 | 5 or 10 or 20 | 5 or 10 or 20 | 5 or 10 or 20 | 5 or 10 or 20 | 5 or 10 or 20 | 5 or 10 or 20 |
| | Type 2 (D antigen units) | 4 or 8 or 16 | — | 4 or 8 or 16 | — | 4 or 8 or 16 | — | 4 or 8 or 16 | — | 4 or 8 or 16 | — | 4 or 8 or 16 | — |
| | Type 3 (D antigen units) | 10 or 16 or 32 | 10 or 16 or 32 | 10 or 16 or 32 | 10 or 16 or 32 | 10 or 16 or 32 | 10 or 16 or 32 | 10 or 16 or 32 | 10 or 16 or 32 | 10 or 16 or 32 | 10 or 16 or 32 | 10 or 16 or 32 | 10 or 16 or 32 |

TABLE 26-continued

| | | Combination Vaccine comprising IPV (Sabin Strain: Type 1, Type 2 & Type 3) | | | | | | | | | | | |
|---|---|---|---|---|---|---|---|---|---|---|---|---|---|
| 7 | Total Aluminium Content ($Al^{3+}$) (as Aluminium Phosphate) | Not more than 0.55 mg | Not more than 0.55 mg | Not more than 0.55 mg | Not more than 0.55 mg | Not more than 0.55 mg | Not more than 0.55 mg | Not more than 0.55 mg | Not more than 0.55 mg | Not more than 0.55 mg | Not more than 0.55 mg | Not more than 0.55 mg | Not more than 0.55 mg |
| 8 | 2-Phenoxyethanol | 2.5 mg | 2.5 mg | 2.5 mg | 2.5 mg | 2.5 mg | 2.5 mg | 2.5 mg | 2.5 mg | 2.5 mg | 2.5 mg | 2.5 mg | 2.5 mg |
| 9 | Methylparaben | — | — | — | — | 0.9 mg | 0.9 mg | 0.9 mg | 0.9 mg | — | — | — | — |
| 10 | Propylparaben | 0.1 mg | 0.1 mg | — | — | 0.1 mg | 0.1 mg | — | — | 0.1 mg | 0.1 mg | — | — |

Additionally adjusting the pH of the composition as disclosed above to about 6.0 to 7.0 with Sodium Hydroxide/Sodium Carbonate and make up the volume by adding normal saline (0.9%). The vaccine may contain traces of glutaraldehyde, formaldehyde, neomycin, streptomycin and polymixin B which are used during the manufacturing process.

Example 2: Manufacturing Process of *Haemophilus influenzae* Type b Conjugate Bulk The broad view of manufacturing steps is presented in FIG. 1 flowchart. Each of the 53 steps of the process is briefly described below:

Step 1: Inoculum State I Shake Flask (S1):

A Working Seed Lot vial is used to inoculate the inoculum stage shake flask, which contains 0.22 μm filtered seed medium. A disposable PETG 125 mL flask with 25 mL working volume is used. This stage is carried out in an incubator shaker with controlled agitation (200±50rpm) and Temperature (36±2° C.). After appropriate bacterial growth is achieved ($OD_{590} \geq 1.0$), the culture is transferred to next inoculum stage (S2 Stage), which is described in step 2. Gram stain is performed as an in-process control to ensure culture purity (Gram negative cocobacilli).

Step 2: Inoculum State II Shake Flask (S2):

S2 inoculum stage consists of 2 L fernbach flasks (S2A and S2B) with 800 mL working volume. S2A flask is used for $OD_{590}$ measurement, till $OD_{590}$ is within acceptance criteria and S2B flask is used for inoculation of S3 stage. Both the flasks are batched with filter-sterilized media, which is identical to the 51 inoculum stage. The 51 stage flask is used to inoculate both the stage II shake flasks. This stage is carried out in an incubator shaker with controlled agitation (200±50 rpm) and Temperature (36±2° C.). After appropriate bacterial growth is achieved ($OD_{590} \geq 1.0$), the culture is transferred to next inoculum stage (S3 Stage), which is described in step 3. Gram stain is performed as an in-process control to ensure culture purity (Gram negative cocobacilli).

Step 3: Inoculum State III Fermentor:

S3 inoculum stage consists of a 120 L fermenter with a 35 L working volume. The fermenter is batched with a media that is identical to the previous inoculum stages. The S2 stage flask is used to inoculate the Inoculum fermentor. Growth is carried out at temperature (36±2° C.), DO (10% set point), agitation (300-600 rpm), aeration (1-5 LPM) and backpressure (0.2 bar) in the inoculum fermenter. After appropriate bacterial growth is achieved ($OD_{590} \geq 1.0$), the culture is transferred to next production stage (S4 Stage), which is described in step 4. Gram stain is performed as an in-process control to ensure culture purity (Gram negative cocobaccilli).

Step 4: 1200 L Scale Production Fermentation:

The 1200 L production fermenter has a working volume of 800 L. It is batched with basal media components and steam sterilized in-situ. Subsequently, various media supplements are added after passing through a 0.22 μm filter. The fermenter is inoculated with S3 stage culture obtained from step 3. The fermentation is carried under controlled dissolved oxygen (20%—set point), temperature (36±2° C.), pH (7.1-7.4), agitation (40-400 rpm), aeration (50-300 LPM) and backpressure (0.2 bar). Two discrete nutrient spikes are added during the course of the fermentation. The growth is monitored by measuring $OD_{590}$ ($OD_{590} \geq 3.5$) and fermentation is considered complete after stationary stage is reached. During growth and stationary phase, the polysaccharide product is secreted and accumulates in the culture broth. Gram stain is performed as an in-process control to ensure culture purity (Gram negative cocobacilli).

Step 5: Formalin Treatment:

Bioburden reduction is achieved in this step by using chemical agent (formalin). 0.1% formalin is added and the fermented broth is incubated for NLT 2 hours at 37° C. After the formalin treatment, the vessel is rapidly cooled to <15° C. Formalin addition is validated to achieve bioburden reduction. This is verified by culture plates after the incubation period. The bioburden reduced broth is ready for harvesting as described in step 6.

Step 6: Continuous Centrifugation Harvest:

Continuous centrifugation is employed as a primary harvest step. This step is performed to separate the polysaccharide containing crude broth from the inactivated biomass. A continuous centrifuge is used with the objective of removing >90% of the biomass, as measured by the $OD_{590}$ reduction. The centrifuge is operated at approximately 15000 g and at a liquid flow rate of 200-500 L/h. The centrifuged supernatant is further processed as described in step 7.

Step 7: 50LP Depth Filtration:

The centrifuged supernatant is passed through a 50LP depth filter to remove coarse material such as cell debris. The step allows the product to pass through the filtrate, and is in-line with an additional depth filter, as described in step 8.

Step 8: 90LP Depth Filtration:

The filtrate from the 50LP depth filter is further passed through a 90LP depth filter (nominal 0.22 μm rating) to further remove any insoluble material that may have not been retained by the previous depth filter. This step ensures that the filtrate is essentially cell-debris free, and can pass through a 0.22 μm filter robustly. The subsequent filtration step is described in step 9.

Step 9 and 10: 0.22 μm Filtration:

The filtrate from the 90LP depth filter is further passed through a 0.22 μm filter, and the filtrate is collected in hold tank.

Step 11 and 12: 100 kD Concentration and Diafiltration:

This step is carried out to remove media components and small molecular weight impurities. In addition, concentration is performed to reduce the working volume. 100 kD molecular weight cut off is chosen as the molecular weight of the Hib polysaccharide (PRP) is ≥500 kD. The broth is concentrated to approximately 10 fold and subsequently diafiltered for NLT 5 volumes using 0.01 M PBS buffer (pH 7.2). The resulting product in the retentate is referred to as "crude PRP" and is further processed as described in step 13. The concentrated broth is transferred to DSP area through transfer port via 0.22 μm filter to ensure that no bacteria is getting carried over to DSP area.

Step 13: CTAB Precipitation:

CTAB (Cetyl-trimethyl ammonium Bromide) is a cationic detergent, which is used for precipitation of polysaccharide. CTAB consists of a hydrophilic region as well as a hydrophobic part, and precipitates protein, nucleic acid and polysaccharide. Crude PRP obtained from step 12 is precipitated at 1% CTAB concentration and incubated for >2 hours.

The CTAB pellet harvesting is described in step 14.

Step 14, 15 and 16: CTAB Pellet Centrifugation, Collection and Storage:

In SEZ-3, FF, CTAB pellet is centrifuged using continuous centrifuge at 15000 rpm. The CTAB pellet is harvested, weighed, aliquoted and stored at ≤−20° C. for further processing. This is the first in-process hold step.

Step 17 and 18: CTAB Paste Thawing and Dissolution:

The frozen CTAB paste is thawed to room temperature. The thawed pellet is dissolved in 5.85% NaCl solution. The dissolution is carried out in a stirred tank and the polysaccharide product is solubilized in the aqueous phase. The tank contains some undissolved material, which comes from precipitated proteins and nucleic acid. This suspension is further processed as described in step 19.

Step 19: Centrifugation:

The material obtained from step 18 is centrifuged at 2-8° C., 5000-6500 rpm for 20-30 minutes to remove the undissolved material. The centrifuged supernatant is collected, and further processed as described in step 20.

Step 20: 72% Ethanol Precipitation:

72% Ethanol is used to precipitate PRP. 96% ethanol is used to generate a final concentration of 72% ethanol with respect to the supernatant obtained in step 19. This precipitation is carried out at 2-8° C. for overnight. The resulting precipitate is harvested as described in step 21.

Step 21 and 22: Centrifugation and Pellet Dissolution:

The 72% ethanol precipitate is collected by centrifugation at 2-8° C., 5000-6500 rpm for 20-30 minutes. The resulting pellet is dissolved in W.F.I. till visual clarity is obtained. Subsequent processing of the solubilized pellet is described in step 23.

Step 23: DOC and 32% Ethanol Precipitation:

To the material obtained from step 22, 6% sodium acetate and 1% sodium Deoxycholate (DOC) is added. 96% ethanol is used to generate a final concentration of 32% ethanol. Both DOC and 32% alcohol drives precipitation of protein impurities, while allowing the polysaccharide to be in the liquid phase. This precipitation is carried out at 2-8° C. for overnight (NLT 8 hrs).

Step 24: Centrifugation:

The material obtained from step 23 is centrifuged at 2-8° C., 5000-6500 rpm for 20-30 minutes to remove the precipitate. The centrifuged supernatant is collected and further processed as described in step 25.

Step 25: Depth and Carbon Filtration:

The supernatant solution obtained in step 24 contains soluble PRP and is subjected to depth filtration followed by carbon filtration to remove nucleic acids and coloring matter. Removal of nucleic acids is monitored by measuring absorbance intermittently at 260 nm ($A_{260}$). After the target $A_{260}$ is reached the solution is filtered through 0.22 μm filter and this filtered solution further processed as described in step 26.

Step 26: 64% Ethanol Precipitation:

The filtered material obtained in step 25 is further precipitated with 96% ethanol at a final concentration of 64% ethanol. This precipitation is carried out at 2-8° C. for overnight. The resulting precipitate is harvested by centrifugation, and further processed as described in step 27.

Step 27: Pellet Collection and Dissolution:

The supernatant is decanted and discarded to collect the pellet. The pellet is dissolved in W.F.I. at room temperature.

Step 28: 300 kD Concentration and diafiltration:

The dissolved pellet solution is concentrated using 300 kD NMWCO membrane. This is further diafiltered not less than (NLT) 8× using W.F.I. The resultant retentate is processed further as described in step 29.

Step 29 and 30: 0.22 μm Filtration and Purified PRP Storage:

The 300 kD UF retentate is passed through an 0.22 μm filter as a clarification step to minimize bioburden. The resulting purified PRP is aliquoted and stored at ≤−20° C. till further use as described in step 31. Sample of purified PRP is sent for Q.C. analysis.

Step 31: Thawing and Pooling:

Based on conjugate batch size appropriate quantity of native polysaccharide obtained from step 30 is thawed. The pooled material is assayed for PRP content, which is required for further processing as described in step 32.

Step 32: 100 kD Concentration:

The pooled purified polysaccharide is required to be of a minimum concentration (8-12 mg/mL) for further processing. If the pool polysaccharide concentration is below the target, pooled polysaccharide solution is concentrated by using a 100 kD UF NMWCO membrane. Sample is drawn after concentration to ensure that the minimum concentration is reached for subsequent steps (step 33).

Step 33: Alkaline Depolymerization:

The concentrated polysaccharide (equivalent to 74 g/110 g) obtained from step 32 is depolymerized under mild alkaline conditions using carbonate-bicarbonate buffer. After target polysaccharide size is reached, the depolymerized polysaccharide is activated as described in step 34.

Step 34: Polysaccharide Activation:

The depolymerized polysaccharide obtained in step 33 is activated using Cyanogen Bromide. This activation is done under nitrogen environment. Cyanogen bromide is highly toxic chemical and appropriate care is taken while handling this chemical.

Step 35: Linker Attachment:

Freshly prepared adipic acid dihydrazide (ADH) solution is added within 6-10 minutes to the reaction mixture obtained from step 34. The reaction is carried out for NLT 16 hours at 2-10° C. The role of the ADH linker is to provide amine groups in polysaccharide required for conjugation reaction.

Step 36: Concentration and Diafiltration:

The reaction mixture obtained from step 35 is concentrated and diafiltered volume by volume with phosphate buffer saline (PBS) using 10 kD NMWCO UF membrane to remove free ADH. The removal of ADH is monitored on HPLC and diafiltration is continued till free ADH level reaches below 5%. The resulting retentate is further diafiltered with NLT 5× MES-NaCl buffer. This is further concentrated to achieve a concentration of NLT 20 mg/mL. This concentrated processed PRP is kept at 2-8° C. till further use as described in step 37.

Step 37 and 38: 0.22 µm Filtration and Processed PRP Storage:

The retentate from step 36 is passed through a 0.22 µm filter, which serves as a clarification step. This also ensures that bioburden levels are controlled during the process, which is performed in grade C area. The filtered activated polysaccharide is collected, sampled, aliquoted and stored at 2-8° C. till further processing. A sample is drawn from the processed polysaccharide pool for analysis, which includes PRP molecular size (kD), PRP content, and PRP degree of activation. Further processing of the processed PRP is described in step 40.

Step 39: TT 10 kD Concentration and Diafiltration:

The conjugation reaction requires two components viz. processed polysaccharide and the carrier protein (TT). The carrier protein is concentrated and diafiltered with MES-NaCl buffer using 10 kD UF NMWCO membrane. This diafiltered carrier-protein is then further concentrated to NLT 20 mg/mL using the same membrane.

Step 40: Conjugation:

The conjugation reaction requires two components viz. processed polysaccharide and the carrier protein (TT). The activated polysaccharide component is obtained from step 38. The carrier protein is obtained from step 39. The two components are mixed in appropriate quantities in the ratio of PRP: TT=1:1 (w/w) in presence of EDC under stirring. The conjugation reaction is monitored on HPLC and is continued till ≥85% conversion of protein (based on the free protein conversion to conjugate) is reached.

Step 41: Quenching:

After the conjugation reaction has proceeded to its acceptance criteria for conversion (step 40), the reaction is terminated by quenching. The conjugation reaction is quenched using phosphate EDTA buffer. This conjugation reaction is subsequently processed as described in step 42.

Step 42: 30 SP and 0.22 Micron Filtration:

The conjugate obtained from step 41 is filtered through a 30 SP filter followed by 0.22 µm filtration. This ensures removal of any large aggregates. The filtered conjugate is processed as described in step 43.

Step 43: 300 kD Ultrafiltration and Diafiltration:

The conjugation reaction mixture obtained from step 42 is diafiltered with 0.05% saline using 300 kD UF NMWCO membrane. The diafiltration is performed to remove conjugation reagents and unreacted TT. The resulting retentate is further processed as described in step 44.

Step 44 and 45: 0.22 um filtration and crude conjugate storage:

The retentate from step 43 is passed through a 0.22 µm filter, which serves as a clarification step. This also ensures that bioburden levels are controlled during the process, which is performed in grade C area. The filtered crude conjugate is collected, sampled and stored at 2-8° C. till further processing. Further processing of the crude conjugate is described in step 46.

Step 46: Crude Conjugate Dilution:

The crude conjugate from step 45 is diluted with W.F.I. to a target concentration of 4±1 mg/mL, if required and further processed by precipitation steps described in step 47.

Step 47: Ammonium Sulphate Precipitation:

The diluted conjugate reaction mixture is further processed to remove free PRP using ammonium sulphate (50% w/v stock solution). The precipitation step is carried out at less than 15° C. under stirring. The precipitation step drives the conjugate in the precipitate, and leaves the free PRP in the supernatant. After addition of ammonium sulphate the resulting suspension is stored at less than 15° C. without stirring for NLT 12 hours.

Step 48: Pellet Collection and Dissolution:

The suspension obtained from step 47 is centrifuged at ~7000 g at 2-8° C. for 40±10 minutes. The supernatant is discarded by decantation and the pellet obtained is dissolved in Tris-saline.

Step 49: 300 kD Diafiltration:

The resulting solution from step 48 is filtered through 30 SP depth filter and diafiltered with 20 mM Tris -Saline using 300 kD NMWCO membrane.

Step 50: GPC Chromatography Purification:

The resulting solution from step 49 is loaded on an approximately 70 L GPC column containing Toyopearl HW-65F hydroxylated methacrylic polymer bead gel for size exclusion chromatography. The use of GPC chromatography for processed conjugate (post-ammonium sulphate) reduces the free PRP levels in the resulting material. The column is eluted with 20 mM Tris 0.9% NaCl, and fractions are collected based on $A_{280}$. Appropriate fractions based on acceptance criteria with respect to free PRP, Ratio and molecular size are pooled, and the pool is further processed, as described in Step 51.

Step 51: 300 kD Diafiltration:

The resulting pooled conjugate eluate from step 50 is diafiltered with 20 mM Tris using 300 kD UF NMWCO membrane. This retentate volume is targeted such that the PRP content in it is approximately 1 mg/mL.

Step 52 and 53: 0.22µm Filtration:

The bulk conjugate obtained from step 51 is filtered through 0.22 µm filter under grade A environment to ensure sterility. The 0.22 µm filter is integrity tested. A sample from the filtered bulk conjugate is sent to Q.C. for complete analysis. The filtered conjugate is labeled as "Sterile Hib Bulk Conjugate" and stored at 2-8° C. Bulk conjugate will be stored at 2-8° C. for maximum up to 3 months and thereafter if unused, it can be stored at −70° C. for total duration up to 1 year.

Quality characteristics of Hib PRP-TT conjugate antigen obtained were as follow:

PRP content (µg/0.5ml): 8.1
Ratio (PRP:TT): 0.5
Free PRP (%): 4.8%
PMW (kD): 983
Avg MW (kD): 752

Example 3: Process of Manufacturing Inactivated wP Antigen

Inactivation Method of Whole Cell Pertussis (wP) Antigen:

Inactivation method optimization is done after performing various experiments which include inactivation at 56° C. for 10min in presence of formaldehyde, 56° C. for 15min in presence of formaldehyde, 56° C. for 10min in presence of hymine, 56° C. for 15min in presence of hymine and only heating at 56° C. for 30min. No significant difference in potency is observed with these methods. Out of these methods, 56° C. for 10min in presence of formaldehyde is selected because pertussis cell mass produced using this method is more homogeneous as compared to other methods mentioned above.

Process of manufacturing inactivated wP antigen comprises the following steps:

a). inactivation at 56° C. for 10-15 minutes in presence of formaldehyde of *Bordetella pertussis* strains 134 b). inactivation at 56° C. for 10-15 minutes in presence of formaldehyde of *Bordetella pertussis* strains 509 c). inactivation at 56° C. for 10-15 minutes in presence of formaldehyde of *Bordetella pertussis* strains 25525 and 6229 c). inactivation at 56° C. for 10-15 minutes in presence of formaldehyde of *Bordetella pertussis* strains 6229 d). subsequently mixing inactivated *Bordetella pertussis* strains 134, 509, 25525 and 6229 in a ratio of 1:1:0.25:0.25.

e). optionally adsorbed onto aluminium based adjuvant.

The process is devoid of thiomersal and inactivated whole cell pertussis antigen remains non-clumpy and homogeneous thereby leading to reduced reactogenicity and giving better potency for a longer duration.

Example 4: Process of Manufacturing Inactivated Polio Virus (IPV)

1. Polio virus may be grown by following method:
   a) CCL81-VERO (Monkey kidney) cell line was used as host cells for the growing of polio viruses i.e. sabin and salk strains.
   b) After infection of host cells with desired strain of polio virus and incubation of 72 hours, the medium containing the virus and cell debris was pooled and collected in a single container.
   c) The filtrate was subjected to tangential flow filtration with 100 KDa cassette; diafiltered using phosphate buffer and purified using anion exchange chromatography.
   d) Prior to administration to patients, the viruses must be inactivated using appropriate inactivation methods.
2. Formalin inactivation comprising of following steps:
   a) The purified virus pool was subjected to buffer exchange from Phosphate buffer to Tris buffer in the range of (30 to 50 mM) having pH between 7 to 7.5,
   b) To the above mixture M-199 medium containing glycine (5 gm/l) was added
   c) 0.025% formaldehyde was added and subsequently mixed,
   d) The mixture was subsequently incubated at 37° C. for 5 to 13 days with continuous stirring of virus bulk on magnetic stirrer,
   e) The post-incubation mixture was subjected to intermediate TFF system (100 KDa, 0.1 m$^2$) on day 7 and final filtration after inactivation
   f) Subsequently the filtered bulk was stored at 2-8° C.,
   g) Performing D-Ag ELISA for D-Ag unit determination
   h) Monovalent pool bulk of IPV type 1, type 2 and type 3 subsequent mixed to form trivalent or bivalent IPV (Salk or Sabin Serotype)
   i) Adjusting the final formulation pH and obtaining final formulation with pH between 6 and 6.8.
   j) The IPV antigen (Sabin or Salk Strains) subsequently added to the final combination vaccine composition adsorbed on the adjuvant (aluminium salt of phosphate) present in the combination vaccine wherein the percentage adsorption of IPV antigen for IPV type 1 was found to be in the range of 10-30%, IPV type 2 in the range of 60-100% and IPV type 3 in the range of 0-25%.
3. Formulation procedure of the IPV (Sabin & Salk Strains) when individually adsorbed onto an aluminium salt:
   a) Taking the desired volume of autoclaved AlPO$_4$ to get the final Alum (Al$^{3+}$) concentration between 0.1 to 0.8 mg/dose in a 50 ml container
   b) Adding IPV bulk with adjusted D-Ag unit and making up the volume with diluent (10× M-199+0.5% Glycine),
   c) Adjusting the final formulation pH and obtaining final formulation with pH between 6 and 6.8.
4) Alum Adsorbed Monovalent Pool Formulated accordingly into Trivalent or Bivalent IPV (Salk or Sabin Serotype)

Results:

Wherein percentage adsorption of IPV type 1, 2, & 3 (Sabin & Salk) onto aluminium phosphate (AlPO$_4$)salt was found to be at least 90%

Applicant has been able to achieve 2 fold dose reduction for polio virus antigens (whereas Standard dose of polio virus antigens is Type 1-40 DU, Type 2-8DU, Type 3-32DU).

TABLE 27

Adsorption studies of Sabin IPV on Alum Phosphate

| | Sample | Titer (per dose) | Virus particles (in K) | % Free in SUP | % Adsorbed on gel |
|---|---|---|---|---|---|
| Type 1, AlPO4 | Control | 5.84 | 691 | NA | |
| | Al$^{3+}$ 125 µg/dose | 3.49 | 3 | 0.43 | 99.57 |
| | Al$^{3+}$ 250 µg/dose | 3.09 | 1.2 | 0.17 | 99.83 |
| | Al$^{3+}$ 500 µg/dose | 2.94 | 0.87 | 0.12 | 99.87 |
| Type 2, AlPO4 | Control | 5.49 | 309 | NA | |
| | Al$^{3+}$ 125 µg/dose | 3.15 | 1.41 | 0.45 | 99.5 |
| | Al$^{3+}$ 250 µg/dose | 3.09 | 1.23 | 0.39 | 99.6 |
| | Al$^{3+}$ 500 µg/dose | 3.09 | 1.23 | 0.39 | 99.6 |
| Type 3, AlPO4 | Control | 5.59 | 389 | NA | |
| | Al$^{3+}$ 125 µg/dose | 5.34 | 218 | 56.04 | 43.94 |
| | Al$^{3+}$ 250 µg/dose | 5.24 | 173 | 44.47 | 55.53 |
| | Al$^{3+}$ 500 µg/dose | 5.16 | 144 | 37.01 | 63.9 |

Example 5: Process of Manufacturing a Combination Vaccine

This example gives a brief of the process of manufacturing a combination vaccine composition comprising D, T, wP, HBsAg, Hib PRP-TT conjugate, IPV and preservative:

Component I—alum adsorbed Diphtheria Toxoid
Component II—alum adsorbed Tetanus Toxoid Component III—wP antigen (as disclosed in Example 3)
Component IV—alum adsorbed Hepatitis B surface Antigen
Component V—Hib PRP conjugate (as disclosed in Example 2)
Component VI—IPV antigen (as disclosed in Example 4)
1. Preparation of component I comprising alum adsorbed Diphtheria Toxoid:
   a). Transfer of aluminium phosphate in the container/vessel
   b). addition of the Diphtheria Toxoid
   c). pH adjustment to 4.5 to 5.5 with Acetic Acid/Sodium Hydroxide
   d). Wait for stabilization
   e). pH adjustment to 5.5 to 6.5 with Sodium Hydroxide/Sodium Carbonate
   f). wait for stabilization
2. Preparation of component II comprising alum adsorbed Tetanus Toxoid:
   a). Transfer of aluminium phosphate in the container/Vessel
   b). addition of the Tetanus Toxoid
   c). pH adjustment to 4.5 to 5.5 with Acetic Acid/Sodium Hydroxide
   d). Wait for stabilization
   e). pH adjustment to 5.5 to 6.5 with Sodium Hydroxide/Sodium Carbonate
   f). wait for stabilization
3. Preparation of component IV comprising alum adsorbed Hepatitis B surface Antigen:
   a). Transfer of aluminium phosphate in the container/Vessel
   b). addition of the Hepatitis B surface Antigen
   c). pH adjustment to 4.5 to 5.5 with Acetic Acid/Sodium Hydroxide
   d). Wait for stabilization
   e). pH adjustment to 5.5 to 6.5 with Sodium Hydroxide/Sodium Carbonate
   f). wait for stabilization
4. Process of manufacturing a combination vaccine composition comprising D, T, wP, HBsAg, Hib PRP-TT conjugate, IPV and preservative
   1. Addition of Normal saline in a blending vessel/container;
   2. Addition of component I
   3. Mixing of Component II in Component I and agitation at RT for 30-45 mins.
   4. Addition of Component III in the above mixture, followed by agitation at RT for 30-60 mins.
   5. Component IV was added to the mixture obtained in step 4 followed by agitation at RT for 30-60 mins.
   6. Component V was added to the mixture obtained in step 5 followed by agitation at 6-16° C. for 30-60 mins.
   7. Component VI was added to the mixture obtained in step 6 followed by agitation at 6-16° C.
   8. Addition of one of the preservative combination disclosed below to the mixture obtained in step 7 at 6-16° C.
      a) 2-Phenoxyethanol in an amount of about 1 mg per 0.5 ml to 6 mg per 0.5 ml (v/v); or
      b) 2-Phenoxyethanol in an amount of about 1 mg per 0.5 ml to 6 mg per 0.5 ml (v/v) and methylparaben used in a concentration of 0.1-1.5 mg per 0.5 ml (w/v); or
      c) 2-Phenoxyethanol in an amount of about 1 mg per 0.5 ml to 6 mg per 0.5 ml (v/v) and propylparaben used in a concentration of 0.05-0.2 mg per 0.5 ml (w/v); or
      d) 2-Phenoxyethanol in an amount of about 1 mg per 0.5 ml to 6 mg per 0.5 ml (v/v), methylparaben used in a concentration of 0.1-1.5 mg per 0.5 ml (w/v) and propylparaben used in a concentration of 0.05-0.2 mg per 0.5 ml (w/v).
   9. Check the pH, if required adjust the pH 6.0 to 7.5 with Sodium Hydroxide/Sodium Carbonate
   10. Make-up the volume with Saline (0.9%) obtained in step 9, followed by agitation for 3 hours.

Example 6: Adsorption, Potency and Stability Profile of Antigens

TABLE 28

This table gives a brief on the percentage adsorption of individual antigens, Potency and Stability profile of individual antigens in SIIPL Combination vaccine at 2-8° C. over a period of 12 months.

| Test | Limits/Specification | 0 Day | 6 Months | 12 Months |
| --- | --- | --- | --- | --- |
| Hepatitis B In-Vivo Potency R.P (95% CL) | (0.61-1.12) | 0.83 | NA | Complies |
| Hib PRP Content (μg/0.5 ml) (Total PRP) | Actual value. | 9.3 μg/0.5 ml | 8.46 μg/0.5 ml | 10.03 |
| Free PRP (%) | | 8 | NA | NA |
| Diphtheria component potency (IU/dose) | NLT 30 IU/dose. | 98.5120 IU/dose (69.9650-137.247) | NA | 95.8463 IU/dose |
| Tetanus component potency (IU/dose) | NLT 40 IU/dose | 139.030 IU/dose (88.2850-208.688) | NA | 382.079 IU/dose |
| Pertussis component potency (IU/dose) | NLT 4 IU/dose | 4.6749 IU/dose (2.6492-8.2763) | 4.8410 IU/dose (2.7331-8.6081) | 5.131 |
| Adsorption Hepatitis-B (%) | Actual value. | 89.44 | 82.65 | 75.52 |

TABLE 28-continued

This table gives a brief on the percentage adsorption of individual antigens, Potency and Stability profile of individual antigens in SIIPL Combination vaccine at 2-8° C. over a period of 12 months.

| Test | Limits/ Specification | 0 Day | 6 Months | 12 Months |
|---|---|---|---|---|
| Adsorption: Tetanus Component (%) | Actual value. | 63.0 | 59.0 | NA |
| Adsorption: Diphtheria Component (%) | Actual value. | 81.0 | 72.0 | NA |
| D Antigen (DU/0.5 ml) (=75% of Nominal value is acceptable) | Type 1 = 20 DU/0.5 ml | 22.414 | Complies | Complies |
| | Type 2 = 4 DU/0.5 ml | 4.692 | Complies | Complies |
| | Type 3 = 16 DU/0.5 ml | 22.084 | Complies | Complies |
| Total Aluminium Content | Not more than 0.6 mg/ 0.5 ml | 0.2768 | NA | NA |

NA—Not available

TABLE 29

Brief on the Percentage adsorption of individual antigens, Potency and Stability profile of individual antigens in Combination vaccine at 25 ± 2° C. over a period of 12 months.

| Test | Limits/ Specification | 0 Day | 6 Months | 12 Months |
|---|---|---|---|---|
| Hepatitis B In-Vivo Potency R.P (95% CL) | NLT 1.0 | Complies | NA | Complies |
| Hib PRP Content (μg/0.5 ml) (Total PRP) | Actual value. | 8.6 μg/ 0.5 ml | 8.20 μg/ 0.5 ml | NA |
| Diphtheria component potency (IU/dose) | NLT 30 IU/dose. | 98.5120 IU/dose (69.9650-137.247) | NA | 96.5482 IU/dose (65.9292-137.687) |
| Tetanus component potency (IU/dose) | NLT 40 IU/dose | 139.030 IU/dose (88.2850-208.688) | NA | NA |
| Pertussis component potency (IU/dose) | NLT 4 IU/dose | 4.6749 IU/dose (2.6492-8.2763) | 4.5170 IU/dose (2.4894-8.2672) | 3.4899 IU/dose (1.8699*-6.4750) |
| Adsorption Hepatitis-B (%) | Actual value. | 89.44 | 83.92 | 83.00 |
| Adsorption: Tetanus Component (%) | Actual value. | 59.0 | 31.0 | 40.0 |
| Adsorption: Diphtheria Component (%) | Actual value. | 79.0 | 72.0 | 69.0 |
| D Antigen (DU/0.5 ml) (=75% of Nominal value is acceptable) | Type 1 = 20 DU/0.5 ml | 22.414 | Complies | Complies |
| | Type 2 = 4 DU/0.5 ml | 4.692 | Complies | Complies |
| | Type 3 = 16 DU/0.5 ml | 22.082 | Complies | Complies |
| Total Aluminium Content | Not more than 0.6 mg/ 0.5 ml | 0.2846 | NA | NA |

NA—Not available

TABLE 30

In-vivo efficacy of Combination vaccine with reduced & standard dose IPV

| | | Poliovirus Type 1 | | | Poliovirus Type 3 | | | |
|---|---|---|---|---|---|---|---|---|
| Sr No | Description | Efficacy | Lower Limt | Upper Limit | Efficacy | Lower Limt | Upper Limit | Result |
| 1 | Hexavalent with 40-8-32 DU IPV | 253.3% | 124.9% | 705.6% | 212.2% | 95.3% | 755.5% | Conform |
| 2 | Hexavalent with 20-4-16 DU IPV | 164.4% | 63.9% | 571.3% | 143.2% | 64.3% | 418.6% | Conform |
| 3 | Hexavalent with 20-4-16 DU IPV | 170.0% | 76.4% | 472.5% | 132.3% | 62.6% | 340.5% | Conform |

TABLE 30-continued

In-vivo efficacy of Combination vaccine with reduced & standard dose IPV

| | | Poliovirus Type 1 | | | Poliovirus Type 3 | | | |
|---|---|---|---|---|---|---|---|---|
| Sr No | Description | Efficacy | Lower Limt | Upper Limit | Efficacy | Lower Limt | Upper Limit | Result |
| 4 | Poliovac with Full dose IPV | 98.5% | 30.9% | 279.4 | 122.8 | 57.3% | 269.8% | Conform |

Observation:
  The Hexavalent vaccine batches manufactured with half dose concentration of IPV has shown promising test results.
  The IPV in-vivo efficacy of the Hexavalent vaccine manufactured at half concentration of IPV was found to be comparable with currently available vaccine (Poliovac in market manufactured by SIIPL) with full dose IPV.

Example 7: Antimicrobial Proficiency Testing

The present inventors, while developing multi-dose combination vaccines containing D, T, wP, Hib, HBsAg, and IPV vaccines, have performed tests on their antimicrobial abilities by adding 2-Phenoxyethanol (2-PE) first, which has been conventionally used as a preservative in the art, in a concentration of 2.5 mg/0.5 ml dose. However, 2-PE was found to have weaker antimicrobial activity than Thiomersal against yeast and fungi in DPT based combination vaccine. An increase of the amount of 2-PE (a preservative) to meet the required criteria may raise safety issues in young children, who are the subjects to receive the vaccine and may also affect the stability of the final products. Further, the amount of preservative(s) to be contained in the vaccines should meet the requirements defined in the US Pharmacopeia, the European Pharmacopeia, the WHO Pharmacopeia, or a combination thereof with respect to the safety of vaccines.

In this regard, the present inventors have performed experiments in an effort to develop a novel composition which can satisfy the requirements on antimicrobial ability by combining the 2-PE with other preservative like Paraben in multi-dose combination vaccine which meets the criteria of both safety and anti-microbial ability. In the present disclosure, the antimicrobial ability test was performed according to the European Pharmacopeia Category B (EP-B) criteria requested by the WHO on vaccine products.

TABLE 31

Details of different combination and concentration of preservatives tested with combination vaccine

| Combinations | 1 | 2 | 3 | 4 | 5 | 6 |
|---|---|---|---|---|---|---|
| Methyl Paraben (MP) | — | 0.18% | 0.18% | 0.18% | — | 0.18% |
| Propyl Paraben (PP) | — | 0.02% | 0.02% | — | 0.02% | 0.02% |
| 2-Phenoxyethanol (PE) | 0.5% | 0.5% | 0.4% | 0.5% | 0.5% | — |

Screening of Antimicrobial Proficiency:
  The Hexavalent combination vaccine preparations as disclosed in Example 1 were inoculated with a total of six microorganisms including four different kinds of bacteria—*Staphylococcus aureus* (ATCC NO.—6538), *Pseudomonas aeruginosa* (ATCC NO.—9027), *Escherichia coli* (ATCC NO.—8739) and *Staphylococcus arlettae* (Environmental isolate EMI); one yeast—*Candida albicans* (ATCC NO.—10231), and one fungus—*Aspergillus brasiliensis* (ATCC NO.—16404) in an amount of $10^5$ to $10^6$ CFU/mL into vaccine preparations at 0 hours, respectively. Then, bacteria, fungi, yeast samples were collected at 0 hours, 24 hours, day 7, day 14 and day 28, cultured in solid media, and the number of colonies was counted between day 3 and day 5 and the log reduction of the colonies was calculated. The results are shown in Table 38 below.

TABLE 32

Antimicrobial proficiency testing Results

| | | CFU recovered/mL of | No Of CFUs Recovered/ml | | | | |
|---|---|---|---|---|---|---|---|
| Sr.No | Culture | positive control(0 hrs) | 24 hrs | $7^{th}$ day | $14^{th}$ day | $28^{th}$ day | Results |
| Formulation 1 0.5% 2PE | S. aureus | $2 \times 10^5$/mL | 87000 | 900 | 0 | — | Conform |
| | P. aeruginosa | $1.8 \times 10^5$/mL | 28000 | 100 | 0 | — | |

TABLE 32-continued

Antimicrobial proficiency testing Results

| Sr.No | Culture | CFU recovered/mL of positive control(0 hrs) | No Of CFUs Recovered/ml | | | | Results |
|---|---|---|---|---|---|---|---|
| | | | 24 hrs | 7$^{th}$ day | 14$^{th}$ day | 28$^{th}$ day | |
| | E. coli | 10 × 10$^5$/mL | 9000 | 0 | — | — | |
| | S. arlettae (EMI) | 2.8 × 10$^5$/mL | 114000 | 1600 | 100 | 0 | |
| | C. albicans | 1.9 × 10$^5$/mL | NA | 400 | 0 | — | |
| | A. brasiliensis | 2.4 × 10$^5$/mL | NA | 1600 | 100 | 0 | |
| Formulation 2 0.5% 2PE + 0.18% MP + 0.02% PP | S. aureus | 2 × 10$^5$/mL | 0 | — | — | — | Conform |
| | P. aeruginosa | 1.8 × 10$^5$/mL | 0 | — | — | — | |
| | E. coli | 10 × 10$^5$/mL | 0 | — | — | — | |
| | S. arlettae (EMI) | 2.8 × 10$^5$/mL | 0 | 0 | — | — | |
| | C. albicans | 1.9 × 10$^5$/mL | NA | 0 | — | — | |
| | A. brasiliensis | 2.4 × 10$^5$/mL | NA | 0 | — | — | |
| Formulation 3 0.4% 2PE + 0.18% MP + 0.02% PP | S. aureus | 2 × 10$^5$/mL | 10 | 0 | — | — | Conform |
| | P. aeruginosa | 1.8 × 10$^5$/mL | 0 | — | — | — | |
| | E. coli | 10 × 10$^5$/mL | 0 | — | — | — | |
| | S. arlettae (EMI) | 2.8 × 10$^5$/mL | 10 | 0 | — | — | |
| | C. albicans | 1.9 × 10$^5$/mL | NA | 0 | — | — | |
| | A. brasiliensis | 2.4 × 10$^5$/mL | NA | 0 | — | — | |
| Formulation 4 0.5% 2PE + 0.18% MP | S. aureus | 2 × 10$^5$/mL | 10 | 0 | — | — | Conform |
| | P. aeruginosa | 1.8 × 10$^5$/mL | 170 | 10 | 0 | — | |
| | E. coli | 10 × 10$^5$/mL | 0 | — | — | — | |
| | S. arlettae (EMI) | 2.8 × 10$^5$/mL | 20 | 0 | — | — | |
| | C. albicans | 1.9 × 10$^5$/mL | NA | 0 | — | — | |
| | A. brasiliensis | 2.4 × 10$^5$/mL | NA | 0 | — | — | |
| Formulation 5 0.5% 2PE + 0.02% PP | S. aureus | 2 × 10$^5$/mL | 20 | 0 | — | — | Conform |
| | P. aeruginosa | 1.8 × 10$^5$/mL | 0 | — | — | — | |
| | E. coli | 10 × 10$^5$/mL | 10 | 0 | — | — | |
| | S. arlettae (EMI) | 2.8 × 10$^5$/mL | 100 | 0 | — | — | |
| | C. albicans | 1.9 × 10$^5$/mL | NA | 0 | — | — | |
| | A. brasiliensis | 2.4 × 10$^5$/mL | NA | 10 | 0 | — | |
| Formulation 6 0.18% MP + 0.02% PP | S. aureus | 2 × 10$^5$/mL | 70000 | 700 | 0 | — | Conform |
| | P. aeruginosa | 1.8 × 10$^5$/mL | 21000 | 0 | 0 | — | |
| | E. coli | 10 × 10$^5$/mL | 6000 | 0 | 0 | — | |
| | S. arlettae (EMI) | 2.8 × 10$^5$/mL | 101000 | 900 | 0 | — | |
| | C. albicans | 1.9 × 10$^5$/mL | NA | 100 | 0 | — | |
| | A. brasiliensis | 1.9 × 10$^5$/mL | NA | 700 | 0 | — | |

NA-Not available;
0.5% 2PE – 2.5 mg/0.5 ml close;
0.4% 2PE – 2 mg/0.5 ml close;
0.18% MP – 0.9 mg/0.5 ml close;
0.02% PP – 0.1mg/0.5 ml close;
CFU- colony forming unit Observation:

It was observed that all Hexavalent vaccine manufactured at different combinations were found to conform the preservative efficacy according to European Pharmacopeia Category B. However, the effectiveness was found to be varied when different combinations were used.

The preservative efficacy of Hexavalent vaccine containing 2PE, MP and PP was found to be very effective as compared to other combinations of preservative viz. Only 2PE, 2PE with PP, 2PE with MP and PP with MP.

It is also noted that preservative efficacy of Hexavalent vaccine containing 0.5% 2PE with PP & MP was found to be more effective as compared with same combinations, but with 0.4% 2PE.

Example 8: SIIPL's Reduced Dose Combination Vaccine vs Easy Six (Panacea)

TABLE 33

This table provides comparison of Percentage adsorption of individual antigens, Potency, Free PRP content between SIIPL's Dose reduced Combination Vaccine and Easy Six (Panacea):

| Tests description | SIIPL Hexavalent vaccine with dose reduced IPV | Panacea Easy-Six ™ combination vaccine with full dose IPV |
|---|---|---|
| HB in vitro potency (µg/ml) | 46.969 | 23.167 |
| HB adsorption (%) | 91.8 | More than 90.0 |
| HB In vivo potency | 1.18 | 0.71(0.42-1.13) |
| Total PRP (µg/0.5 ml) | 9.18 | 13.20 |
| Free PRP (%) | 9.0 | 19.45 |
| Free formaldehyde (% W/V) | 0.0011 | 0.0011 |
| 2-PE (% W/V) | 0.499 | 0.660 |
| Diphtheria Adsorption (%) | 82 | 38 |
| Tetanus adsorption (%) | 63 | 30 |

TABLE 33-continued

This table provides comparison of Percentage adsorption of individual antigens, Potency, Free PRP content between SIIPL's Dose reduced Combination Vaccine and Easy Six (Panacea):

| Tests description | SIIPL Hexavalent vaccine with dose reduced IPV | Panacea Easy-Six ™ combination vaccine with full dose IPV |
|---|---|---|
| Type 1 (DU/0.5 ml) | 22.414 | 43.504 |
| Type 2 (DU/0.5 ml) | 4.692 | 8.056 |
| Type 3 (DU/0.5 ml) | 22.084 | 39.84 |
| Aluminium (mg/dose) | 0.2846 | 0.6034 |
| In vivo Efficacy IPV Type-1 | 170.0% | Not tested |
| IPV Type-3 | 132.3% | |
| Diphtheria Potency | 98.5120 IU/dose (69.9650-137.247) | More than 40 |
| Tetanus Potency | 139.030 IU/dose (88.2850-208.688) | More than 50 |
| Pertussis potency | 4.6749 IU/dose (2.6492-8.2763) | 3.2221 (1.8032-5.7706) |

We claim:

1. A process of manufacturing a fully liquid multi-dose immunogenic composition wherein 0.5 ml of the composition comprises:
   (i) a diphtheria toxoid, (D) in an amount of 10 Lf to 25 Lf, adsorbed onto aluminium salt having percentage adsorption of at least 50%;
   (ii) a tetanus toxoid, (T) in an amount of 2 Lf to 10 Lf, adsorbed onto aluminium salt having percentage adsorption of at least 40%;
   (iii) an inactivated whole cell pertussis, (wP) containing inactivated *Bordetella pertussis* strains 134, 509, 25525 and 6229 in a ratio of 1:1:0.25:0.25, in an amount of 12 IOU to 16 IOU;
   (iv) a hepatitis B virus surface antigen, (HBsAg) in an amount of 7 µg to 15 µg, adsorbed onto aluminium salt having percentage adsorption of at least 50%;
   (v) a *Haemophilus influenzae* type b antigen, (Hib) in an amount of 7 µg to 13 µg;
   (vi) an inactivated polio virus antigen, (IPV) containing IPV Type 1 in an amount of 1-25 DU, IPV Type 2 in an amount of 1-10 DU or IPV Type 3 in an amount of 1-20 DU; and
   (vii) total aluminium adjuvant content ($Al^{3+}$) in a range of 0.1 mg to 0.6 mg; and
   (viii) preservative as 2-phenoxyethanol in an amount of 1-6 mg (v/v); methylparaben in an amount of 0.1-1.5 mg (w/v) and propylparaben in an amount of 0.05-0.2 mg (w/v); or
   2-phenoxyethanol in an amount of 1-6 mg (v/v) and methylparaben in an amount of 0.1-1.5 mg (w/v); or
   2-phenoxyethanol in an amount of 1-6 mg (v/v) and propylparaben in an amount of 0.05-0.2 mg (w/v);
   the process comprising the steps of:
   a). Addition of 80% of total Normal saline (NaCl) in a blending vessel/container;
   b). Addition of Component-I comprising Diphtheria Toxoid in a blending vessel/container;
   c). Addition of Component-II comprising Tetanus Toxoid to Component-I of Step-b) with agitation at room temperature;
   d). Addition of Component-III comprising inactivated whole cell pertussis antigen to a mixture obtained in Step-c) with agitation at room temperature;
   e). Addition of Component-IV comprising Hepatitis B surface Antigen to mixture obtained in Step-d) at room temperature;
   f). Addition of Component-V comprising Hib Antigen to the mixture obtained in Step-e) at 6-16° C. .;
   g). Addition of Component-VI comprising IPV antigen to the mixture obtained in Step-f) at 6-16° C. .;
   h). Addition of a preservative combination selected from:
   2-Phenoxyethanol in an amount of 1 to 6 mg per 0.5 ml (v/v) and methylparaben in an amount of 0.1-1.5 mg per 0.5 ml (w/v); or
   2-Phenoxyethanol in an amount of 1 to 6 mg per 0.5 ml (v/v) and propylparaben in an amount of 0.05-0.2 mg per 0.5 ml (w/v); or
   2-Phenoxyethanol in an amount of 1 to 6 mg per 0.5 ml (v/v), methylparaben in an amount of 0.1-1.5 mg per 0.5 ml (w/v) and propylparaben in an amount of 0.05-0.2 mg per 0.5 ml (w/v);
   i). Adjusting pH of the mixture obtained in Step-h) to 6.0 to 7.0 with Sodium Hydroxide/Sodium Carbonate; and
   j). Adding remaining 20% total normal saline (NaCl) to make up a volume with agitation.

2. The process as claimed in claim 1, wherein preparation of the component I comprises the following steps:
   a). Transfer of Aluminium phosphate in the blending vessel/container;
   b). Addition of the Diphtheria Toxoid;
   c). pH adjustment to 4.5 to 5.5 with Acetic Acid/Sodium Hydroxide;
   d). hold the mixture obtained in step (c) at 33-37° C. for at least 48 hours;
   e). pH adjustment to 5.5 to 6.5 with Sodium Hydroxide/Sodium Carbonate; and
   f). stabilization with histidine buffer.

3. The process as claimed in claim 1, wherein preparation of the component II comprises the following steps:
   a). Transfer of Aluminium phosphate in the blending vessel/container;
   b). addition of the Tetanus Toxoid;
   c). pH adjustment to 4.5 to 5.5 with Acetic Acid/Sodium Hydroxide;
   d). hold the mixture obtained in step (c) at 33-37° C. for at least 48 hours;
   e). pH adjustment to 5.5 to 6.5 with Sodium Hydroxide/Sodium Carbonate; and
   f). stabilization with histidine buffer.

4. The process as claimed in claim 1, wherein preparation of the component III comprises the following steps:
   a). inactivation at 56° C. for 10-15 minutes in presence of formaldehyde of *Bordetella pertussis* strains 134;
   b). inactivation at 56° C. for 10-15 minutes in presence of formaldehyde of *Bordetella pertussis* strains 509;
   c). inactivation at 56° C. for 10-15 minutes in presence of formaldehyde of *Bordetella pertussis* strains 25525 and 6229;
   c).
   d). subsequently mixing inactivated *Bordetella pertussis* strains 134, 509, 25525 and 6229 in a ratio of 1:1:0.25:0.25; and
   e). optionally adsorbed onto aluminium based adjuvant;
   wherein the process is devoid of thiomersal and inactivated whole cell pertussis antigen remains non-clumpy and homogeneous.

5. The process as claimed in claim 1, wherein preparation of the component IV comprises the following steps:
   a). Transfer of aluminium phosphate in the blending vessel/container;

b). addition of the Hepatitis B surface Antigen;
c). pH adjustment to 4.5 to 5.5 with Acetic Acid/Sodium Hydroxide;
d). hold the mixture obtained in step (c) at 33-37° C. for at least 48 hours;
e). pH adjustment to 5.8 to 6.8 with Sodium Hydroxide/Sodium Carbonate; and
f). stabilization.

6. The process as claimed in claim 1, wherein preparation of Component-V comprises the following steps:
a). Fermentation of *Haemophilus influenzae* Type b;
b). Inactivation at 37° C. for 2 hours in presence of 0.1% formaldehyde;
c). Purification of Hib polyribosylribitol phosphate (PRP) polysaccharide;
d). Conjugation of purified product of step c to tetanus toxoid (TT) using a Cyanogen Bromide cyanylation conjugation chemistry in presence of adipic acid dihydrazide (ADH) linker;
e). purification of conjugate of step d; and
f). filtration of purified conjugate preferably through 0.22 μm filter;
wherein a percentage free PRP is no more than 5% in a total purified Hib bulk conjugate.

7. A fully liquid multi-dose immunogenic composition, wherein 0.5 ml of the composition comprises one of the following:
a) D antigen in an amount of 10 Lf; T antigen in an amount of 2 Lf, wP antigen in an amount of 12 IOU; HBsAg in an amount of 8 μg; Hib antigen in an amount of 8 μg; IPV antigen, type 1 (Mahoney strain) in an amount of 20 DU, type 2 (MEF-1 strain) in an amount of 4 DU or type 3 (Saukett strain) in an amount of 16 DU, respectively; total aluminium content ($Al^{3+}$) not more than 0.55 mg; 2-Phenoxyethanol in an amount of 2.5 mg (v/v); or
b) D antigen in an amount of 20 Lf; T antigen in an amount of 4 Lf; wP antigen in an amount of 14 IOU; HBsAg in an amount of 15 μg; Hib antigen in an amount of 10 μg; IPV antigen, type 1 (Mahoney strain) in an amount of 20 DU, type 2 (MEF-1 strain) in an amount of 4 DU and type 3 (Saukett strain) in an amount of 16 DU, respectively; total aluminium content ($Al^{3+}$) not more than 0.55 mg; 2-Phenoxyethanol in an amount of 2.5 mg (v/v); or
c) D antigen in an amount of 25 Lf; T antigen in an amount of 10 Lf; wP antigen in an amount of 16 IOU; HBsAg in an amount of 15 μg; Hib antigen in an amount of 13 μg; IPV antigen, type 1 (Mahoney strain) in an amount of 20 DU, type 2 (MEF-1 strain) in an amount of 4 DU and type 3 (Saukett strain) in an amount of 16 DU, respectively; total aluminium content ($Al^{3+}$) not more than 0.55 mg; 2-Phenoxyethanol in an amount of 2.5 mg (v/v); wherein the composition is prepared by the following process:
a). Addition of 80% of total Normal saline (NaCl) in a blending vessel/container;
b). Addition of Component-I comprising Diphtheria Toxoid in a blending vessel/container;
c). Addition of Component-II comprising Tetanus Toxoid to Component-I of Step-(b) with agitation at room temperature;
d). Addition of Component-III comprising inactivated whole cell pertussis antigen to mixture obtained in Step-(c) with agitation at room temperature;
e). Addition of Component-IV comprising Hepatitis B surface Antigen to mixture obtained in Step-(d) at room temperature;
f). Addition of Component-V comprising Hib Antigen to the mixture obtained in Step-(e) at 6-16° C. .;
g). Addition of Component-VI comprising IPV antigen to the mixture obtained in Step-(f) at 6-16° C. .;
h). Addition of 2-Phenoxyethanol to the mixture obtained in Step-(g) at 6-16° C.
i). Adjusting pH of the mixture obtained in Step-(h) to 6.0 to 7.0 with Sodium Hydroxide/Sodium Carbonate; and
j). Adding remaining 20% of total normal saline (NaCl) to make up a volume with agitation.

8. The composition as claimed in claim 7, wherein the preparation of the component I comprises the following steps:
a). Transfer of Aluminium phosphate in the blending vessel/container;
b). Addition of the Diphtheria Toxoid;
c). pH adjustment to 4.5 to 5.5 with Acetic Acid/Sodium Hydroxide;
d). hold the mixture obtained in step (c) at 33-37° C. for at least 48 hours;
e). pH adjustment to 5.5 to 6.5 with Sodium Hydroxide/Sodium Carbonate; and
f). stabilization with histidine buffer.

9. The composition as claimed in claim 7, wherein the preparation of the component II comprises the following steps:
a). Transfer of Aluminium phosphate in the blending container/vessel;
b). addition of the Tetanus Toxoid;
c). pH adjustment to 4.5 to 5.5 with Acetic Acid/Sodium Hydroxide;
d). hold the mixture obtained in step (c) at 33-37° C. for at least 48 hours;
e). pH adjustment to 5.5 to 6.5 with Sodium Hydroxide/Sodium Carbonate; and
f). stabilization with histidine buffer.

10. The composition as claimed in claim 7, wherein the preparation of the component III comprises the following steps:
a). inactivation at 56° C. for 10-15 minutes in presence of formaldehyde of *Bordetella pertussis* strains 134;
b). inactivation at 56° C. for 10-15 minutes in presence of formaldehyde of *Bordetella pertussis* strains 509;
c). inactivation at 56° C. for 10-15 minutes in presence of formaldehyde of *Bordetella pertussis* strains 25525 and 6229;
d). subsequently mixing inactivated *Bordetella pertussis* strains 134, 509, 25525 and 6229 in a ratio of 1:1:0.25:0.25; and
e). optionally adsorbed onto aluminium based adjuvant;
wherein the process is devoid of thiomersal and inactivated whole cell pertussis antigen remains non-clumpy and homogeneous.

11. The composition as claimed in claim 7, wherein the preparation of the component IV comprises the following steps:
a). Transfer of aluminium phosphate in the blending vessel/container;
b). addition of the Hepatitis B surface Antigen;
c). pH adjustment to 4.5 to 5.5 with Acetic Acid/Sodium Hydroxide;
d). hold the mixture obtained in step (c) at 33-37° C. for at least 48 hours;

e). pH adjustment to 5.8 to 6.8 with Sodium Hydroxide/ Sodium Carbonate; and f). stabilization.

12. The composition as claimed in claim 7, wherein the preparation of Component-V comprises the following steps:

a). Fermentation of *Haemophilus influenzae* Type b;

b). Inactivation at 37° C. for 2 hours in presence of 0.1% formaldehyde;

c). Purification of Hib polyribosylribitol phosphate (PRP) polysaccharide;

d). Conjugation of purified product of step c to tetanus toxoid (TT) using a Cyanogen Bromide cyanylation conjugation chemistry in presence of adipic acid dihydrazide (ADH) linker;

e). purification of conjugate of step d; and f). filtration of purified conjugate preferably through 0.22 μm filter;

wherein a percentage free PRP is no more than 5% in a total purified Hib bulk conjugate.

* * * * *